United States Patent
Doshi et al.

(10) Patent No.: US 8,920,287 B2
(45) Date of Patent: Dec. 30, 2014

(54) METHOD AND SYSTEM FOR PROVIDING FITNESS ACTIVITY TRACKING AND GAMING

(75) Inventors: Anil Doshi, New York, NY (US); Michael Howsden, Salt Lake City, UT (US)

(73) Assignee: Introplay LLC, New York, NY (US)

( * ) Notice: Subject to any disclaimer, the term of this patent is extended or adjusted under 35 U.S.C. 154(b) by 1208 days.

(21) Appl. No.: 11/833,745

(22) Filed: Aug. 3, 2007

(65) Prior Publication Data

US 2008/0033581 A1 Feb. 7, 2008

Related U.S. Application Data

(60) Provisional application No. 60/835,793, filed on Aug. 4, 2006.

(51) Int. Cl.
*A63B 24/00* (2006.01)

(52) U.S. Cl.
USPC ........................................ 482/8; 482/1; 482/9

(58) Field of Classification Search
USPC ........................................ 482/1–9, 900–902
IPC ........................................................ A63B 24/00
See application file for complete search history.

(56) References Cited

U.S. PATENT DOCUMENTS

| | | | |
|---|---|---|---|
| 4,463,946 A | 8/1984 | Wallace et al. | |
| 4,842,275 A | 6/1989 | Tsatskin | |
| 4,918,603 A | 4/1990 | Hughes et al. | |
| 5,018,736 A | 5/1991 | Pearson et al. | |
| 5,149,084 A | 9/1992 | Dalebout et al. | |
| 5,158,093 A | 10/1992 | Shvartz et al. | |
| 5,263,723 A | 11/1993 | Pearson et al. | |
| 5,362,069 A | 11/1994 | Hall-Tipping | |
| 5,366,427 A | 11/1994 | Price, II | |
| 5,713,793 A | 2/1998 | Holte | |
| 5,788,283 A | 8/1998 | Adler | |
| 5,830,069 A | 11/1998 | Soltesz et al. | |
| 5,846,132 A | 12/1998 | Junkin | |
| 5,860,862 A | 1/1999 | Junkin | |
| 5,971,854 A | 10/1999 | Pearson et al. | |
| 6,007,426 A | 12/1999 | Kelly et al. | |
| 6,135,881 A | 10/2000 | Abbott et al. | |
| 6,292,706 B1 | 9/2001 | Birch et al. | |
| 6,319,123 B1 | 11/2001 | Paludi | |
| 6,371,855 B1 | 4/2002 | Gavriloff | |
| 6,443,904 B2 | 9/2002 | Nissilä | |
| 6,688,978 B1 | 2/2004 | Herman | |
| 6,918,860 B1 | 7/2005 | Nusbaum | |
| 6,945,911 B2 | 9/2005 | Jackowski | |

(Continued)

OTHER PUBLICATIONS

Kristen Nicole; IntroPLAY launches Community to Track Workouts; Web-Ad; May 11, 2007; http://mashable.com/2007/05/11/introplay.com.

(Continued)

*Primary Examiner* — Glenn Richman
(74) *Attorney, Agent, or Firm* — Ditthavong & Steiner, PC

(57) ABSTRACT

An approach is provided for tracking and analyzing physical activities. Inputs are received from a plurality of users. The inputs specify one or more physical activities. The inputs are analyzed to quantitatively compare the activities among the users. A score is assigned to each user based on the analysis. The scores can be presented to the users over a communication network.

8 Claims, 29 Drawing Sheets

(56) References Cited

U.S. PATENT DOCUMENTS

| | | | |
|---|---|---|---|
| 2003/0006557 A1* | 1/2003 | Busch | 273/292 |
| 2005/0187644 A1* | 8/2005 | Neale et al. | 700/91 |
| 2006/0178765 A1* | 8/2006 | Graepel et al. | 700/91 |
| 2007/0060325 A1* | 3/2007 | Gradek | 463/29 |
| 2007/0135243 A1* | 6/2007 | LaRue et al. | 473/467 |
| 2007/0191110 A1* | 8/2007 | Crouse | 463/43 |

OTHER PUBLICATIONS

Rosario Doriott; Get off the couch, Five ways to get your sport on this summer; Web-Blog; Jun. 27, 2007; http://sportsillustrated.cnn.com/2007/sioncampus/06/25/internet.sports/index,html.

Introplay; Exercising the Wii, Jan. 16, 2008; One Million Minutes, Nov. 29, 2007; New Activity and Hiking Intensites, Nov. 22, 2007; Kids and Exercise, Oct. 29, 2007; IntroPLAY Now on Facebook Platform, Oct. 23, 2007; New Features in introPLAY, Oct. 22, 2007; Keep Your Friends Healthy, Oct. 7, 2007;Don't Believe Everything You Read and Hear about Health, Sep. 17, 2007; Multivitamin Daily Vital, Aug. 23, 2007; Trophy Room Launch, Aug. 20, 2007 https://introplay.wordpress.com.

Diet Blog, Weight Loss Forums and Social Networks; Diet Blog; Lifestyle Health & Fitness; Metropolitan Statistical Area; Body to Soul Fitness; http://www.diet-blog.com/archives/2006/12/28/weight_loss_forums_and_social_networks.php.

Steven V. Dubin; Get Fit Fast Through Motivational Team Based Fitness Challenge; Apr. 22, 2005; http://www.theopenpress.com/index.php?a=press& id=1426.

Weight Loss Challenge, Competition & Online Weight Loss Programs; Lose weight and keep it off . . . Forever; 2004-2008 WeightLossWars; http://www.weightlosswars.com.

Salt Lake City Gets Fit; Jun. 16, 2007; http://www.slcgetsfit.com.

* cited by examiner

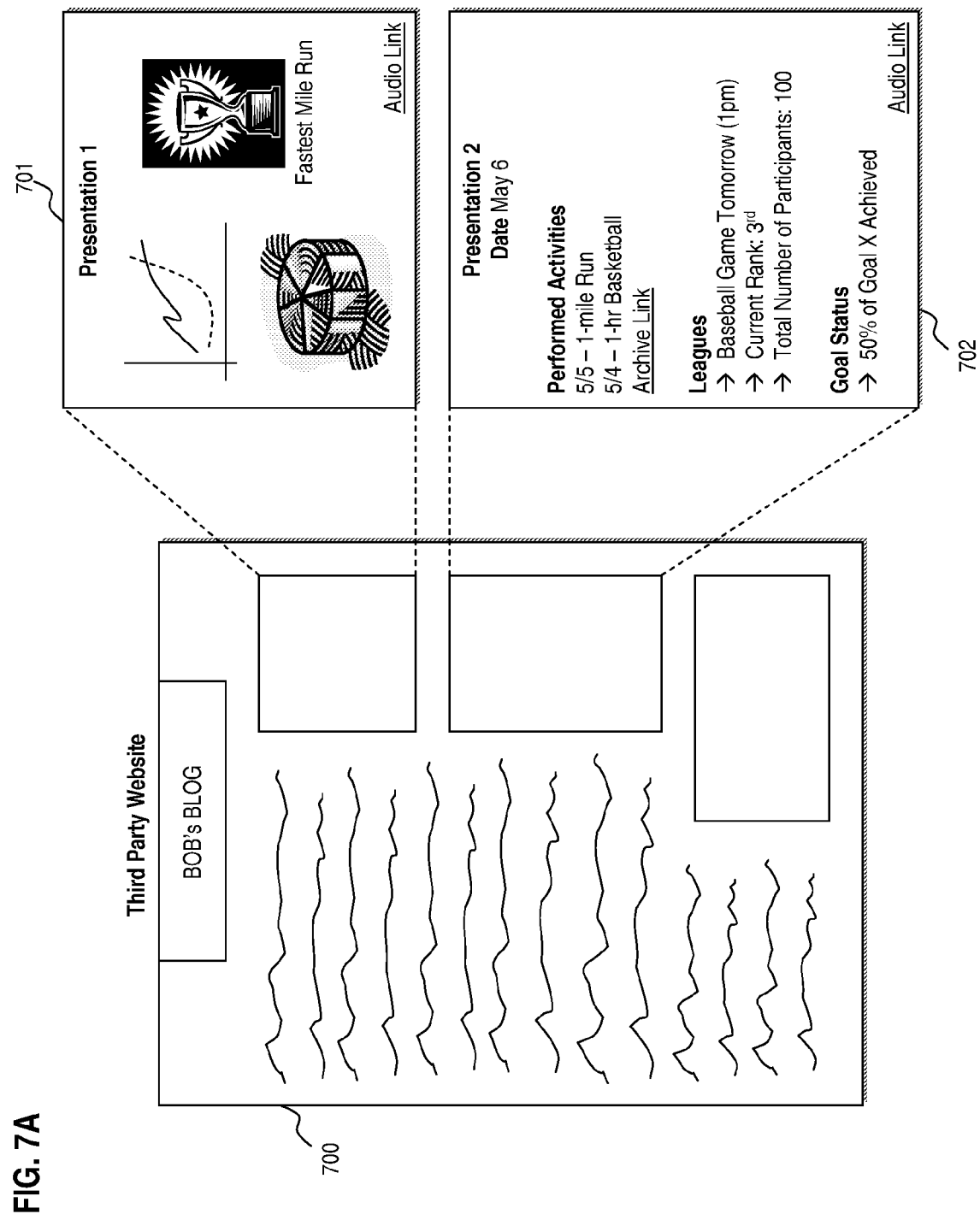

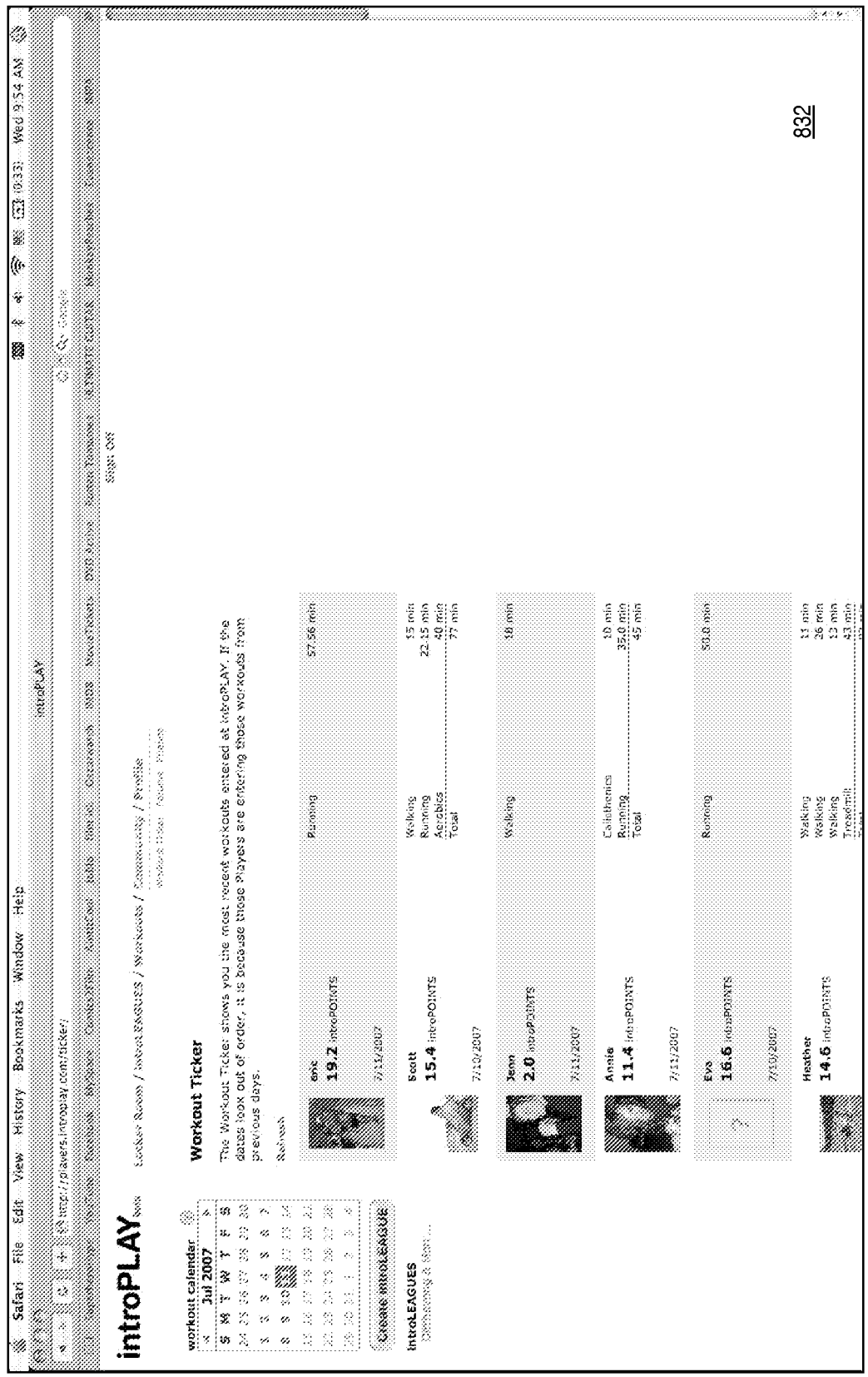

METHOD AND SYSTEM FOR PROVIDING FITNESS ACTIVITY TRACKING AND GAMING

RELATED APPLICATIONS

This application claims the benefit of the earlier filing date under 35 U.S.C. §119(e) of U.S. Provisional Application Ser. No. 60/835,793, filed Aug. 4, 2006, entitled "Method and System for Providing Fitness Activity Tracking and Gaming"; the entirety of which is incorporated by reference.

FIELD OF THE INVENTION

The present invention relates to activity tracking, and more particularly to monitoring physical activities and gaming associated with such activities.

BACKGROUND OF THE INVENTION

It is undisputed that physical fitness needs to be more integrated into modern living. Obesity has reached epidemic proportions, affecting millions of adults and children. While carrying excess body fat can decrease an individual's overall quality of life, being overweight also leads to adverse metabolic effects on one's blood pressure, cholesterol, triglycerides, and insulin resistance. Studies have shown that the overweight possess an increased risk of developing and worsening medical conditions like diabetes, cardiovascular disease, hypertension, stroke, osteoarthritis, sleep apnea, and even certain forms of cancer, especially the hormonally related and large-bowel types. Not surprisingly, adult obesity contributes to a large number of adult deaths per year in the United States alone, and imparts a staggering cost for healthcare related services.

Although heredity plays an important role in determining an individual's susceptibility to weight gain, the ultimate determination is contingent upon an energy balance considering one's caloric intake against their level of physical exertion. In this regard, effective weight management should include a steady commitment to a well-balanced diet and a regular exercise regimen. Accordingly, those committed to such lifestyles often experience a myriad of benefits including reduced health care costs, increased productivity, better performance on the job and at school, lower absenteeism and turnover, not to mention increased participation in social activities. However, most people understand these benefits but instead choose to forgo them for a sedentary, malnourished lifestyle. At the root of the problem with disinterest in physical activity is a general lack of motivation.

Moreover, even individuals who do not have a weight problem know that physical activity is a key to good health and generally want to be motivated to engage in physical activity for their own well-being. Even those individuals who are already highly motivated would like to have a better statistical understanding of their physical profile.

Therefore, there is a need for an environment that encourages, as well as motivates, individuals to engage in physical activity and for an environment that is instructive regarding an individual's physical activity goals.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 7A and 7B illustrate, respectively, a third party publication (such as a "web log" or simply "blog") implementing various embodiments of the present invention, and a third party blog administration site implementing an embodiment of the present invention;

DESCRIPTION OF THE PREFERRED EMBODIMENT

A system, method, and software for tracking and analyzing physical activities are described. In the following description, for the purposes of explanation, numerous specific details are set forth in order to provide a thorough understanding of the present invention. It is apparent, however, to one skilled in the art that the present invention may be practiced without these specific details or with an equivalent arrangement. In other instances, well-known structures and devices are shown in block diagram form in order to avoid unnecessarily obscuring the present invention. Further, the many aspects, features, and advantages of the present invention are readily apparent from the following detailed description, simply by illustrating a number of particular embodiments and implementations, including the best mode contemplated for carrying out the present invention. The present invention is also capable of other and different embodiments, and its several details can be modified in various obvious respects, all without departing from the spirit and scope of the present invention. Accordingly, the drawings and description are to be regarded as illustrative in nature, and not as restrictive.

Figure 1:
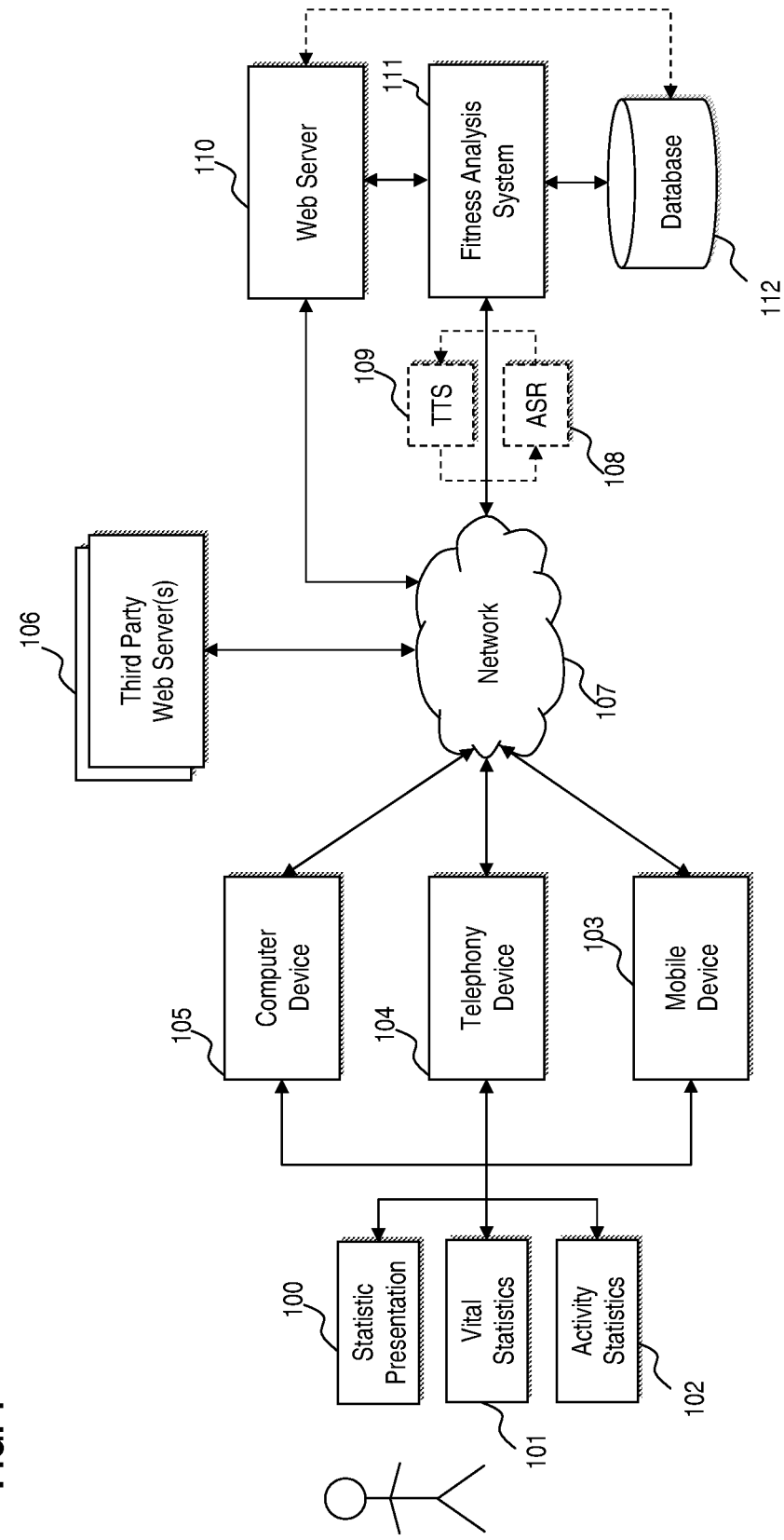
FIG. 1 is a diagram of a system for providing tracking and analysis of fitness activities, according to one embodiment of the present invention.

FIG. 1 is a diagram of a system for providing tracking and analysis of physical activities, according to one embodiment of the present invention. It is noted that a plethora of exercise equipment exists for weight loss, for improving stamina, and for strength training. Further, these devices typically include various telemetric outputs that monitor a user's level of exertion including a pulse monitor, a distance meter, a rate monitor, a time monitor, a strain gauge, an accelerometer and/or other sensors that measure physical performance. Furthermore, these machines generally accept user specific data such as age, weight, and desired resistance. In turn, the exercise equipment can generate personalized outputs such as calories burned, heart rate maintained, and fitness levels met. However, all of this detailed data is activity and user specific. In other words, any given machine can only monitor user performance independently from other machines used or activities engaged in. It is not practical to create a quantitative comparison across a multitude of cross-training activities and, therefore, a determination of effort expended and overall fitness level achieved cannot be made. Moreover, there is no opportunity for comparison against historical performances or other individual's data. As such, exercisers cannot readily determine a level of improvement, assess whether long term goals were achieved, or compete against other individuals.

Additionally, exercising can be a rather dull, tedious activity that requires a great level of devotion to stay committed. For most, their willpower is quickly overborne by the monotony of routine. Often this occurs because the exerciser does not have any encouragement or external influence to motivate them. There is no sense of competition, cooperation, support, or enjoyable aspect to give them a reason to continue.

A fitness analysis system 111 of FIG. 1 allows a user to enter and be presented with extensive details for personal vital and activity statistics, using data modules 100, 101 and 102, respectively, for a multitude of sports activities, and exercises as well as non-sport activities (e.g., daily activities such as eating and sleeping habits, etc.)—collectively referred to as "activities." Further, the system 111 allows users to review input data, at 100, as well as appraise various reports generated by the fitness analysis system 111, in accordance with the various embodiments of the present invention. Data may be collected across multiple users (e.g., a community of users) and aggregated for analysis, manipulation, and presentation.

In this manner, a user can enter a variety of vital statistics, via module 101, including information relating to daily activities, health statistics, and general outlook parameters.

Daily activities may include eating habits (number of meals and types of foods eaten, calories consumed, nutritional content, etc.), hours of sleep/work/play, whether dietary supplements (vitamins, protein shakes, herbal extracts, etc.) were taken, number of cigarettes smoked or alcoholic drinks consumed, glasses of water drank, and the like. Health statistics may include age, height, weight, weight distribution among various tissues (muscle, fat, bone and marrow, internal organs, connective tissue and skin, blood), body measurements and weight distribution (head, neck, trunk, arms, legs), water content, area of skin, heart rate (resting), blood pressure (systolic, diastolic), cholesterol, glucose, triglycerides, high density lipoproteins (HDL), low density lipoproteins (LDL), bioimpedance, body mass index (BMI), and the like. Outlook parameters might comprise subjective determinations regarding perceived energy level, happiness, stress, soreness, etc. While daily activities and health statistics have predefined values given the nature of the information to be entered, subjective outlook parameters must be quantified. Some form of a scale system is suiting. For example, the scale system for happiness might numerically range from one to five, one representing a low sentiment level and five representing a high sentiment level. However, embodiments of the present invention are not limited only to number scales. For example, the scale system for soreness could correlate to a range of smiling to frowning faces or a range of color intensities as well as other scales known in the art.

Meanwhile, activity statistics, as provided via module 102, relate to an individual's actual performance in each respective activity executed. Activity statistics may include activity performed, traversed distance, time, exercising heart rate (pulse), cycles, repetitions, sets, resting period, etc. The data may be entered as totals, averages, and/or distributions over time, intensity, activity, distance, or other perceivable ratio. Furthermore, the activity statistics are also envisioned to be activity specific like number of points in basketball, innings played in baseball, number of tackles in football, etc. An initial set of activities is presented below in Table 1, however, it should be appreciated that this set may be added to and, therefore, should not be considered exhaustive.

TABLE 1

Initial Set of Activities

| | | | |
|---|---|---|---|
| Aerobics | Badminton | Baseball | Basketball |
| Beach Volleyball | Bicycling | Boxing | Broomball |
| Calisthenics | Canoeing | Cheerleading | Cricket |
| Cross Country Skiing | Cross Training | Curling | Dance |
| Diving | Dodgeball | Downhill Skiing | Elliptical Trainer |
| Fencing | Field Hockey | Figure Skating | Football |
| Golf | Gymnastics | Handball | Hiking |
| Ice Hockey | Ice Skating | Jai Alai | Judo/Jujitsu |
| Karate | Kayaking | Kick Boxing | Kickball |
| Kung Fu | Lacrosse | Mountain Climbing | Orienteering |
| Paddleball | Pilates | Polo | Portaging |
| Racquetball | Rock Climbing | Rollerblading | Roller Skating |
| Rope Jumping | Rowing | Rugby | Running |
| Scuba Diving/Skin Diving | Skateboarding | Ski Jumping | Ski Machine |
| Snorkeling | Snow Shoeing | Snowboarding | Soccer |
| Softball | Speed Skating | Squash | Stair Training |
| Stair Treadmill | Stationary Bicycling | Stationary Rowing | Stretching |
| Surfing | Swimming | Synchronized Swimming | Tae Kwon Do |
| Tai Chi | Tennis | Track and Field | Treadmill Running |
| Ultimate Frisbee | Volleyball | Walking | Wallyball |
| Water Aerobics | Water Jogging | Water Polo | Water Skiing |
| Water Volleyball | Weight Training | Whitewater Rafting | Wrestling |
| Yoga | | | |

In order to input this vast amount of information into the system 111, a user may optionally utilize any one of a computer 105, telephony 104, or mobile device 103 available. Computer devices 105 can include one of a desktop computer, notebook computer, server, terminal, workstation, customized hardware, or the like. Telephony devices 104 may include one of a plain-old-telephone, wireless telephone, cellular telephone, satellite telephone, voice over internet protocol telephone, fax machine, etc. Mobile devices 103 may include a personal digital assistant, a pocket personal computer, a smart phone, a tablet, a handset, customized hardware, or other mobile device capable of transmitting data and/or voice protocols.

Within the broad realm of devices available, many methods of data entry exist. These methods include, but should not be limited to website entry (data fields, pull-down menus, radio button selections, scalars, checkboxes, etc.), instant messaging, electronic mail, text messaging, specifically designed software application entry, facsimile, voice transmission, postal mailing, and/or the like. As such, a user has the ability to input data in a plain-text, standard language (or near equivalent) format. When input in this format, transmissions will be parsed into the appropriate data parameters by the fitness analysis system 111. Further, data may be entered in one device using one of the above methods and then synchronized to another for transmission.

Further, when a user transmits data in a voice format, the system 111 may optionally include a text-to-speech (TTS) engine 109 and/or an automatic speech recognizer (ASR) engine 108 for converting analog to digital signals and vice versa. As such, when a user interacts with the fitness analysis system 111 using voice transmission the ASR 108 converts a user's spoken language (analog signal) into textual form (digital signal) for processing by the fitness analysis system 111. Meanwhile, the TTS engine 109 converts textual information (digital signal) from fitness analysis system 111 to speech (analog signal) for playback to the user. In this manner, a user may interact with fitness analysis system 111 receiving and sending information using voice protocols, e.g., voice extensible markup language (VXML) programs. Those skilled in the art will recognize that optionally provided TTS 109 and ASR 108 engines may be collocated or integrated within fitness analysis system 111 or the network 107. Further, TTS 109 and ASR 108 functionality can be implemented on one of the various input devices, e.g., 103, 104, 105 that are available to the user.

Also, a web server 110, or equivalent online system, can be utilized to permit the user to interface with the fitness analysis system 111. The web server 110 may be optionally linked to the database 112 for more efficient extraction of stored vital and activity statistics, 101 and 102, respectively. Moreover, the web server 110 can communicate with one or more third party web servers 106, or equivalent online systems, via network 107 to provide users another method of interaction with the fitness analysis system 111. In this manner, the present invention can be embedded into, linked with and/or pushed to various online environments. An example of such capability is described later with respect to FIGS. 7A and 7B.

Thus, from the above description, those skilled in the art should appreciate that the user is not confined to any single method or device for data input. Namely, the user can utilize any combination of methods and/or devices available. Furthermore, the above methods and devices can be implemented in various physical environments, e.g., at user's home or work, at public gym, at recreational center, at strategically placed kiosks, etc. In this regard, users may be allowed to input data temporally close to the time it was collected.

Transmission of user specific vital and activity statistics to the fitness analysis system 111 is provided via network 107. In the various embodiments of the present invention, network 107 may comprise a telephony network, data network, wireless network, or any combination thereof. Accordingly network could comprise the public switched telephone network (PSTN), the Internet, an Intranet, a local area network (LAN), a wide area network (WAN), a cellular network, a satellite network, etc.

The system 111 is configured to allow users to enter, track, manipulate, and analyze detailed vital and activity statistic data across a multitude of activities. This fitness analysis system 111 is further coupled to a database 112 for storing user data. Although only a single database 112 is shown, the functionality may be distributed among various databases in a database management system. Further, the database 112 can be collocated with or integrated within fitness analysis system 111. The functional capabilities of the fitness analysis system 111 are more fully described with regard to FIG. 2.

Figure 2:
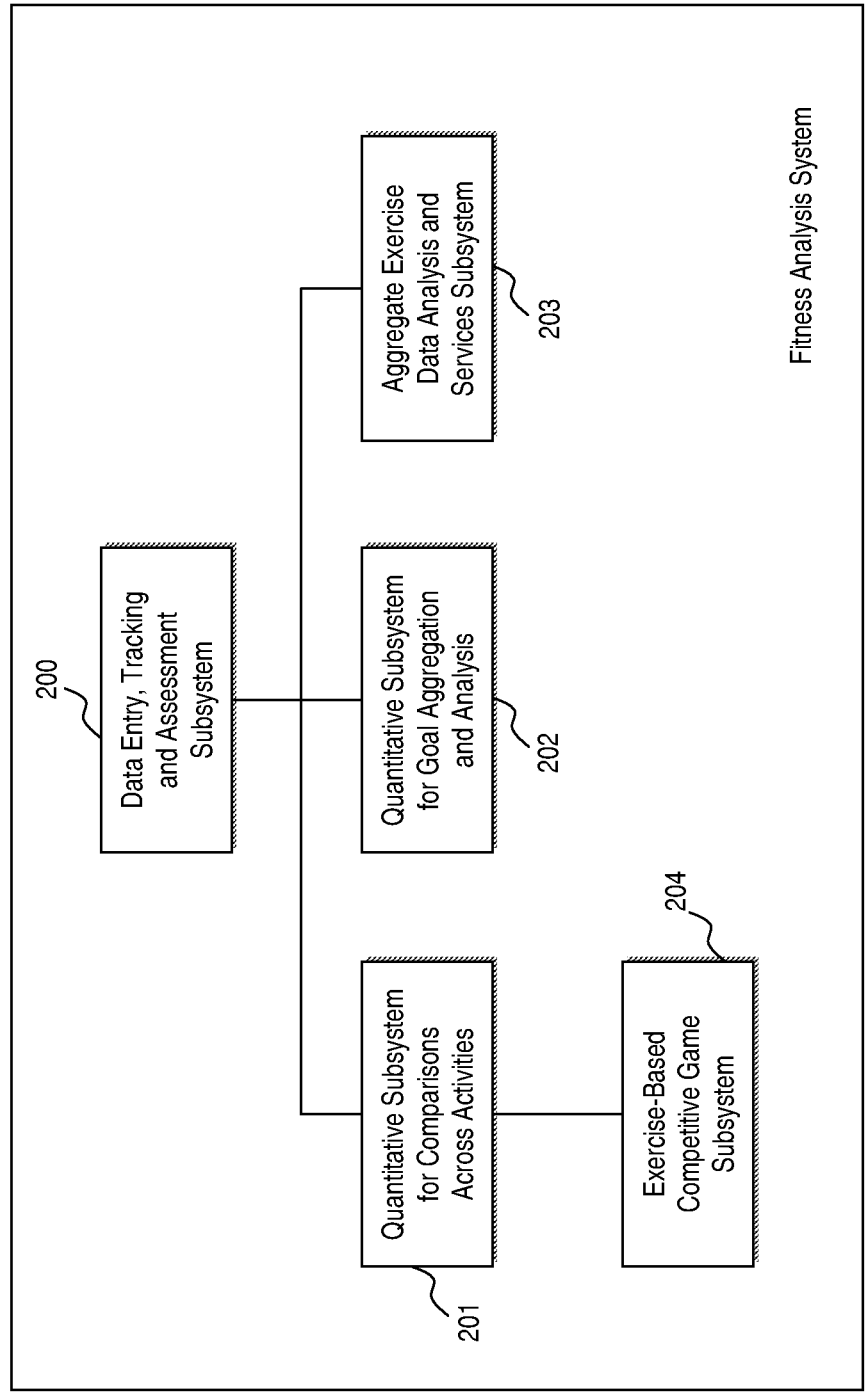
FIG. 2 is a diagram of an exemplary fitness analysis system of FIG. 1, in accordance with an embodiment of the present invention.

FIG. 2 is a diagram of an exemplary fitness analysis system 111 of FIG. 1, in accordance with an embodiment of the present invention. The system 111 contains various subsystems 200, 201, 202, 203, and 204 for carrying out various embodiments of the present invention. The data entry, tracking, and assessment subsystem (DTA) 200 allows users to enter and track detailed vital and activity statistics in tremendous depth across a multitude of activities and statistical parameters, as explained above. DTA 200 parses user transmitted data into appropriate parameter fields and distributes the parsed data between the other subsystems—i.e., Quantitative Subsystem for Comparisons Across Activities 201, Quantitative Subsystem for Goal Aggregation and Analysis 202, Aggregate Exercise Data Analysis and Services Subsystem 203, and Exercise-Based Competitive Game Subsystem 204—for aggregation, utilization, manipulation, and analysis. Further, DTA 200 accepts data from these other subsystems for generating reports for users to track their performance. Such reports can be transmitted in visual and/or audio formats. Visual reports might include charts, graphs, lists, tables, text, etc. Audio reports can be explained versions of the visual reports, including recorded audio, human translation, computer generations, and the like.

DTA 200 also communicates with database 112 for data storage and recall.

Figure 3:
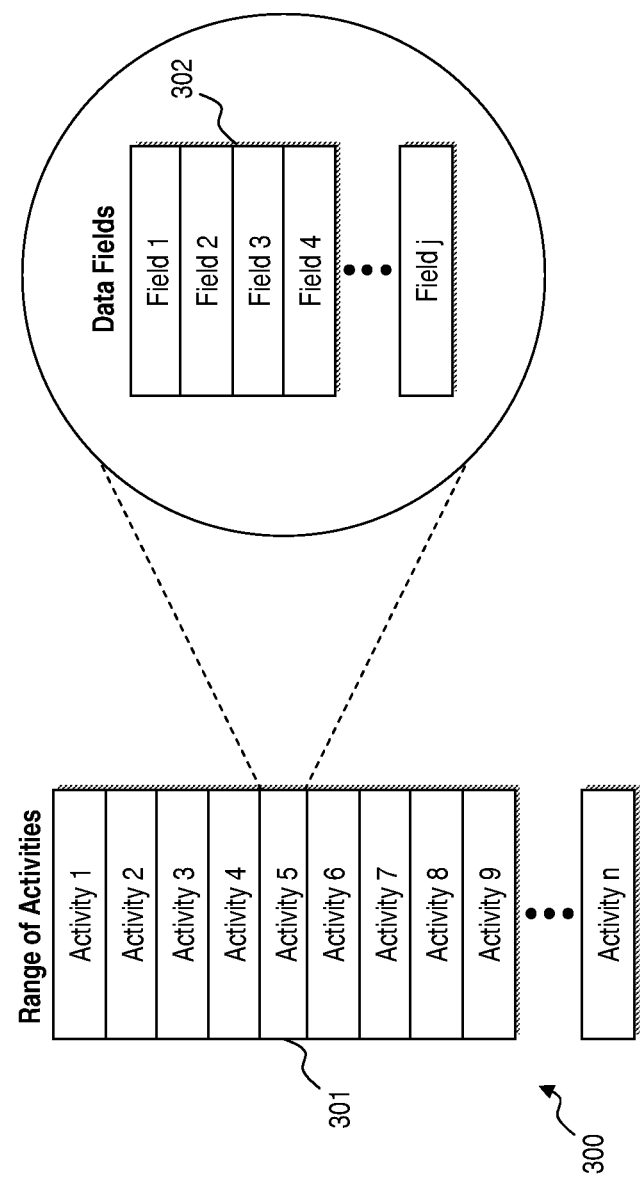
FIG. 3 is a diagram of a data structure utilized by the database of FIG. 1, according to one embodiment of the present invention.

FIG. 3 depicts an exemplary embodiment of a data structure that can be used by the database 112 of FIG. 1, in accordance with an embodiment of the present invention. As in typical database management systems, data can be stored in one or more data containers, each container contains records, and the data within each record is organized into one or more fields. As shown in FIG. 3, a data container 300 is correlated to the range of activities a user can participate in, e.g., from 1 to n (n being an integer) activities correlating at least to the list provided within Table 1. Further, each activity 301 may be broken down into data fields 302, e.g., 1 to j correlating to the various activity dependent parameters that the user can enter. In this regard, the number of data fields, j, may also be dependent upon the level of detail that the user would like to maintain. Hence, it is possible for two users to enter the same workout differently, based upon the desired amount of information storage. Using a 30 minute running activity as an example, one user may enter a 30 minute run at moderate intensity, whereas another user may enter a 10 minute, 1 mile warm-up at light intensity, a 10 minute, 1.75 mile interval run at medium intensity, and a 10 minute, 1-mile cool down walk at a low intensity. Moreover, depending on the number of vital statistics users want to store in relation to the activities performed, an infinite range of possible field values are possible.

Additionally, while the number of data fields, j, can be predefined by system operators, users may also dynamically create optional data fields for more detail or remove data fields for less detail. In this case, users may submit changes, additions, amendments, and deletions to the database structure 112 through fitness analysis system 111 using known methods. Such an editing process ensures that fitness analysis system 111 is tracking the most appropriate, pertinent data as delineated by the actual user. This ensures users will remain interested as they determine the effort level necessary to maintain their associated database.

For certain activities, the database 112 may allow a user to search for possible activities 301 as well as fields 303 for data entry. This is helpful for users who choose to participate in various physical activities, but are not experts. In this manner, users who are unfamiliar with activities, terminology, types of resistances, muscle groups, body positions, motions, techniques, or practices can search under these categories to browse for new parameters and/or activities to store data under. Further, individuals can use sort-reduction or filtered menu options to narrow the list of possible choices at each successive inquiry. Such a method of data entry and storage represents an improvement over existing data entry and tracking methods because the user no longer has to know the name of the activity he/she is engaging in nor the requisite data fields to be entered.

For example, a novice exerciser might know that his/her shoulders are weak and desire an exercise to build this muscle. The user might search under shoulder exercises and learn that this type of activity can be achieved through bodybuilding, stationary rowing, playing basketball, etc. The user might inquire under bodybuilding to a list of muscle groups comprising the shoulder muscle, e.g., the deltoid or the various heads of the deltoid muscle including the anterior, lateral, and posterior heads. Still further, the user could inquire under the lateral head of the deltoid muscle and acquire a list of possible exercises that involve that muscle, e.g., seated dumbbell raises, lateral raises, military press, clean and press, etc. The user could then choose the lateral raise exercise and learn specific details concerning that exercise, e.g., techniques, motions, handgrips, etc., as well as specific parameters for data entry—i.e., sets, repetitions, weight used, resting period, etc. Included within each of these categories can be an encyclopedic link to an information store that the novice exerciser could further search under to learn about the terminology, requirements, or other specifics of the activity. For instance, the user could learn preparatory steps for the exercise, execution methods, comments, warnings, classifications, involved forces, mechanics, utility, etc. In this manner, the fitness analysis system 111 serves as a learning/educational tool as much as it serves as a data store.

Further, those skilled in the art should appreciate that the database 112 can be configured using other known methods. For instance, in relational database systems, the data containers would be referred to as tables, the records referred to as rows, and the fields referred to as columns. In object-oriented databases, the data containers 300 would be referred to as object classes, the records referred to as objects, and the fields referred to as attributes. Other database architectures may use other terminology. As such, systems that implement the present invention are not limited to any particular type of data container 300 or database 112 architecture. However, for the purpose of explanation, the terminology and examples used herein shall be that typically associated with relational databases. Thus, the terms "table," "row," and "column" shall be used herein to refer respectively to the data container, record, and field.

Referring back to FIG. 2, the fitness analysis system 111 also comprises a quantitative subsystem for comparing data across activities (QCD). This allows a user to quantify his/her exerted effort in each activity on a normalized scale. As such, the user can quantify a total workout detailing the level of exertion across all the activities performed as well as their temporal position within the workout schedule. Moreover, the user can compare his/her performance against historical performances as well as against other users.

In one embodiment, the comparison may be achieved by assigning a base point value, e.g., 10 points, for an activity performed over a predefined period of time. This base value can be equal to a typical, average, or conventional length of time for performing a particular activity by an average athlete. For example, a 30-year old male athlete of average ability can be assigned 10 points for running 1.5 miles in 12.5 minutes. While the base values for each activity can be predetermined, they can also be "learned" by the fitness analysis system 111 using previously aggregated data entered into the system 111. This might be accomplished, for example, through the use of software algorithms or by conventional data analysis. Thus, the fitness analysis system 111 can more accurately gauge what is "typical" for the athletes actually using the system 111.

Further, the base values can be adjusted for the relative skill of the particular user. By including a second dimension such as intensity, athletes of lesser ability can be assigned relative points values for completing the same activity as a greater athlete. For instance, an athlete of less than average ability will perceive a 12.5 minute, 1.5 mile run as more intensive than an athlete of higher then average ability. As such, the relative skill level of the athlete should affect the point value assigned for completing the same activity. Accordingly, the more skilled individual can be assigned fewer points for completing the same activity as the less skilled individual.

In this manner, the QCD 201 can involve adjusting a relative length of time engaged in an activity by an intensity multiplier to arrive at an assigned point value per activity completed. However, for some activities like golf, weightlifting, or calisthenics, length of time may be respectively exchanged with values like number of holes played, number of sets performed, or number of repetitions executed. As such, because the QCD 201 standardizes the point value based on effort put forth on an activity-by-activity basis, the QCD 201 can eliminate possible biases associated with using only standardized parameters like calories or time.

It is noted that if only calories were used as a comparison, the results would be skewed towards activities that were more calorie-intensive than others. For instance, if one were to compare running to weightlifting, an athlete might burn more calories running, but the total benefit to each respective exerciser can be the same. Yet the results would be skewed towards running as being more beneficial. Likewise, if only time were used as a comparison, a similar distortion might occur. For example, playing 18-holes of golf in three hours might take more time than swimming for 35 minutes. As a result, using time alone would skew the results toward golf as being more beneficial to an individual. Thus, the QCD 201 is an improvement over other systems that do not normalize data between activities before comparing the results.

By using the normalized results of QCD 201, in certain embodiments of the present invention, the fitness analysis system 111 can establish an exercise-based competitive game. Referring back to FIG. 2, exercise-based competitive game subsystem (EBG) 204 is provided so as to accept normalized/standardized results from the QCD 201. In this manner, users may access the fitness analysis system 111 to record their activities, receive numerical points for their effort, and view their point totals relative to their own historical performances as well as to other individuals. Further, points can be awarded for certain dietary behaviors, e.g., limiting caloric intake to 2000 calories per day, eating fifteen fruits and vegetables per week, substituting soda products for juice, etc. Accordingly, users may be categorized as individual participants or further grouped into teams. Thus, the combined efforts of many can be aggregated into a league so as to provide a sense of competition between users. Since individuals may be grouped onto teams, users can also feel a sense of accountability since their team is dependent on the various members for scoring points. Moreover, participants can be motivated to score more points by exercising more or maintaining a healthier lifestyle to ensure their team is the best.

Figure 4:
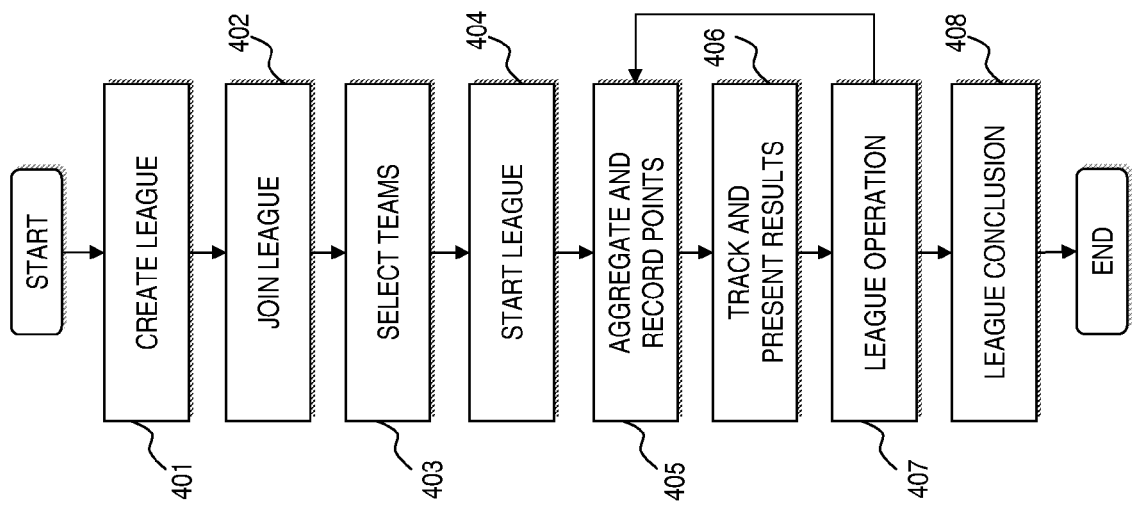
FIG. 4 is a flowchart of a process for establishing an exercise-based competitive game, according to an embodiment of the present invention.

FIG. 4 illustrates a flowchart of a process for establishing an exercise-based competitive game league in according with the present invention. The competition begins when an individual logs into the fitness analysis system 111 and initiates a league, per step 401, by setting up a database to accept data for certain activities and parameters associated with those activities, as explained above. Further, the league initiator may determine the length of play (including a start and end date) or the number of individuals per team; establish privacy settings; create criteria for joining the league, per step 402; customize the scoring system; set the availability of certain league functionality; etc.

With regard to customizing the scoring system, a league initiator may allow or exclude points for certain activities. For instance, drinking eight glasses of water a day might relate to a bonus point or smoking a cigarette might decrease an individual's score by a point. Further, league initiators may develop their own metric for scoring other than that proffered above. As an example, points can be assessed on the variety of activities performed per workout, or basketball points scored, hours of activity contributed, etc. League functionality might include the ability to set up a draft for selecting teams, trading players, establishing activity disputes, assessing penalties, creating rules, allowing for midseason modifications, etc.

Once the league has been initiated, participants may be allowed to join the league, per step 402, according to any predefined parameters established by the league initiator. In this regard, the process of joining the league may be by invitation only, whether by the organizer and/or current members, or available to anyone. Special leagues could be limited to friends, coworkers, teammates, family members, or be as expansive as a global community. After joining, participants are allowed to further customize league parameters based on the functionality allowed for by the league initiator.

As shown in FIG. 4, teams are selected per step 403 according to a predefined method, e.g., randomly, at the discretion of the league initiator, by a draft system, a team selection process, or any combination thereof. Specifically regarding the team selection process, the league initiator might designate captains for choosing participants to be on their team. Captains could also be selected by a voting, nomination, or volunteer system. When the captains are designated, they might pick and choose participants in an asynchronous draft format to select teams, as in step 403. This might require captains to rank the remaining members of the league according to their ability, interests, personality, etc. Participant rankings might also be implemented automatically when an athlete joins the league. After ranking, a draft system might randomly assign a choosing order for team captains to select teammates or might establish the choosing order and then automatically select teams by assigning unassigned participants to the teams based on their individual rank. When the teams are established, the league will commence, per step 404, on the start date, as shown.

Next, certain league operations can be performed, per step 407, during the operation of the league. These aspects might include trading players, dropping out, adding new players, disputing the validity of another individual's recorded activities, establishing a team name, communicating with individuals in the league via a messaging system on a website, e-mails, telephone calls, facsimile, or other means known in the art. This may represent a change in teams or point assessments, thus, the process of FIG. 4 may selectively repeat the appropriate steps for aggregating and recording points, per step 405, according to the new league parameters.

At this point, the league is active and users can continually record activities and associated parameters according the previously described methods, per step 406. Moreover, activities can be aggregated and points assessed by QCD 201 and passed onto EGB 204 for determining an individual's contribution to his or her score as well as the score for that individual's team. Further data can be shared with the quantitative subsystem for goal aggregation and analysis (GAA) 202 for goal assessment and the aggregate exercise data analysis and services subsystem (DAS) 203 of FIG. 2 for data analysis and service operations. The GAA 202 and DAS 203 subsystems are more fully described below.

The league is concluded, per step 408, on the established end date, and the process is ended. At this point, a system of records across all individual participants and/or teams can be established to determine which individual(s)/team(s) had the best statistical performance in each data field and/or other calculated data entry point. From these results, the fitness analysis system 111 can send a notification to participants to recognize the effort put forth by these participants. Such recognition might take the form of a textual bracket, team standings, graphic trophy, etc.

Figure 5:
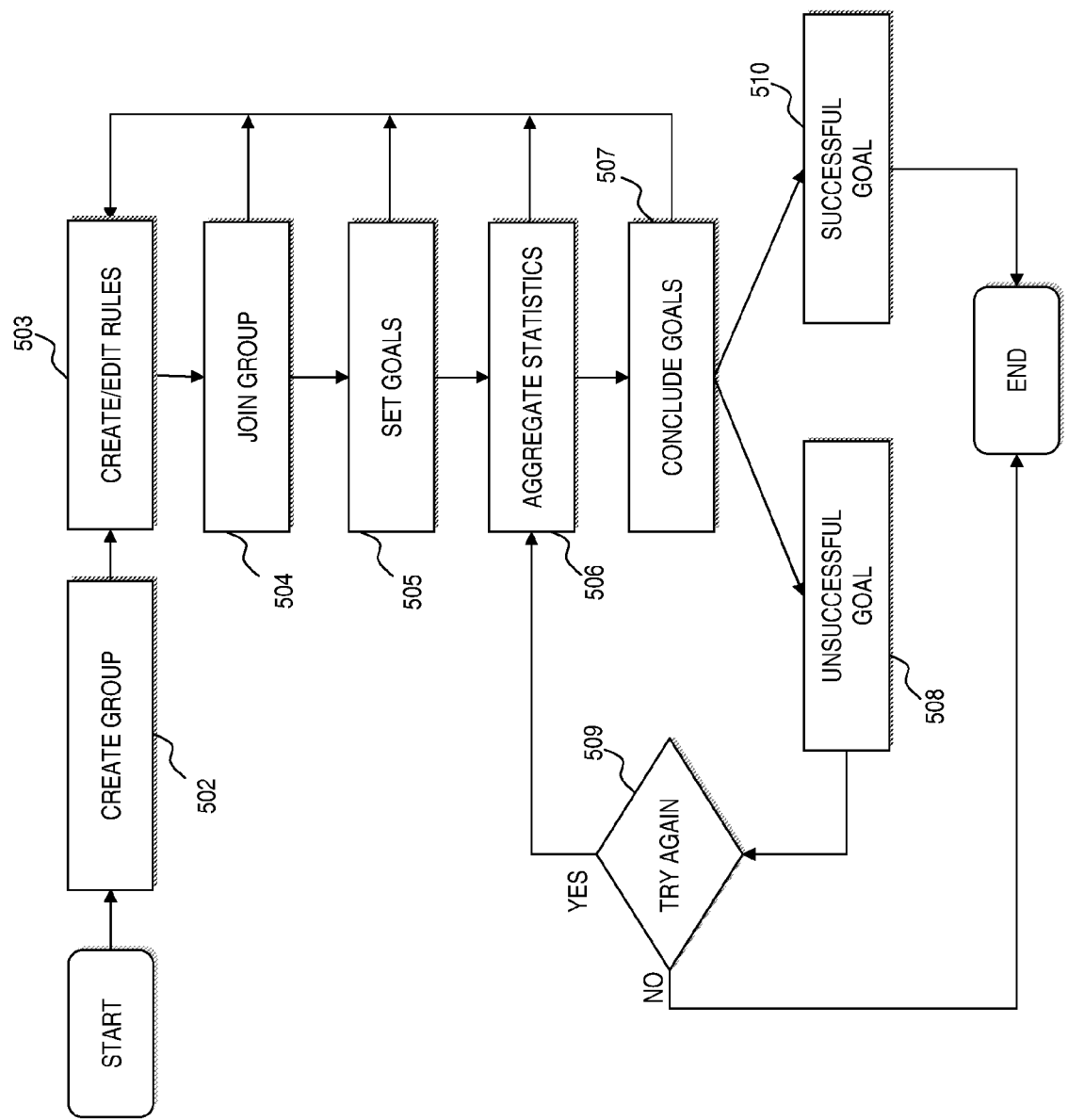
FIG. 5 is a flowchart of a process for establishing, maintaining, and assessing goals, according to an embodiment of the present invention.

FIG. 5 is a flowchart of a process for establishing, maintaining, and assessing goals, according to an embodiment of the present invention. As shown in FIG. 5, individuals can form groups (or teams), per step 502, and have the option to create, monitor, and assess one or more individual and/or group goals. Referring back to FIG. 2, this functionality is provided by the quantitative subsystem for goal aggregation and analysis (GAA) 202. GAA 202 allows one or more individuals to work towards one or more exercising goal(s) wherein each individual's effort contributes towards the overall achievement. In this manner, individuals are provided yet another motivating factor. Moreover, since the goals can be team oriented, each participant will feel a sense of accountability to the team for ensuring successful goal achievement.

After individuals form groups consisting of at least one participant, per step 502, the participants can establish certain rules and parameters for themselves and/or their group, per step 503, such as name, logo, motto, public or private membership, to whom leadership will be assigned, to whom goal setting tasks will be allocated, approval rights, etc. These rules and parameters may be added to, eliminated, or otherwise modified over time.

With the rules in place, and individuals having joined groups, as in step 504, one or more participants of the group can establish goals, per step 505, based on the various vital and activity statistics described earlier. Accordingly, the goals can be ephemeral, long term, and/or recursive. Further, the goals can be defined through multiple parameters such as a goal name, timing requirements, activity requirements, maintaining certain statistic measures within and among activities, sustaining certain dieting regimes, etc. per step 506. For example, a three member team might set a treadmill running goal requiring participants to run at least five miles per workout, at a medium intensity, enter average heart rate after each workout, all the while attempting to run 400 miles within a 30 day time limit. Further, goals might intertwine or otherwise correlated to one another. For example, dependent team goals can be 100 hours of overall exercising or overall team weight loss of 50 pounds. When a set time limit, for example, has expired, goals are concluded (step 507) and a determination is made as to whether a goal was successful, per step 510, or unsuccessful, per step 508. If unsuccessful, it is determined, per step 509, whether a participant would like to try again. If not, the process is ended. If the determination is affirmative, then aggregate statistics are collected again per step 506.

Additionally, since GAA 202 is configured to be cyclic, while one goal is in progress or concludes, one or more other goals can be created and tracked independently or simultaneously. However, at the conclusion of each goal, GAA 202 will determine whether the goal was successfully achieved. If unsuccessful, GAA 202 allows individuals and/or teams to reinstate the goal. This provides motivation for participants to keep trying and pushing forward in their efforts for a better lifestyle. Groups formed within the GAA 202 can exist for finite or infinite durations. A user who is a participant in one or more EBG 204 leagues can also be a participant in one or more GAA 202 groups. Moreover, the EBG subsystem 204 has the ability to incorporate GAA functionality within league play to provide yet another hierarchical level of motivation and competition. For instance, teams might not only compete for the highest overall score, but may also compete to determine who can complete an established goal the fastest or most efficiently. Further, goals can be established across various teams or team members.

Referring back to FIG. 2, the fitness analysis system 111 also provides aggregate exercise data analysis and supplemental services through the aggregate exercise data analysis and services subsystem (DAS) 203. DAS 203 is configured to provide real-time data analysis to the users across various activities and within select groups of individuals. As such, the DAS 203 can compare and contrast tracked vital and/or activity statistics across the activities and individuals. As described above, this real-time analysis can be provided to the users in both visual as well as audible formats. In this manner, DAS 203 passes the analysis to DTA 200 for transmission back to the user at one of the various devices associated with the user, shown in FIG. 1.

Figure 6:
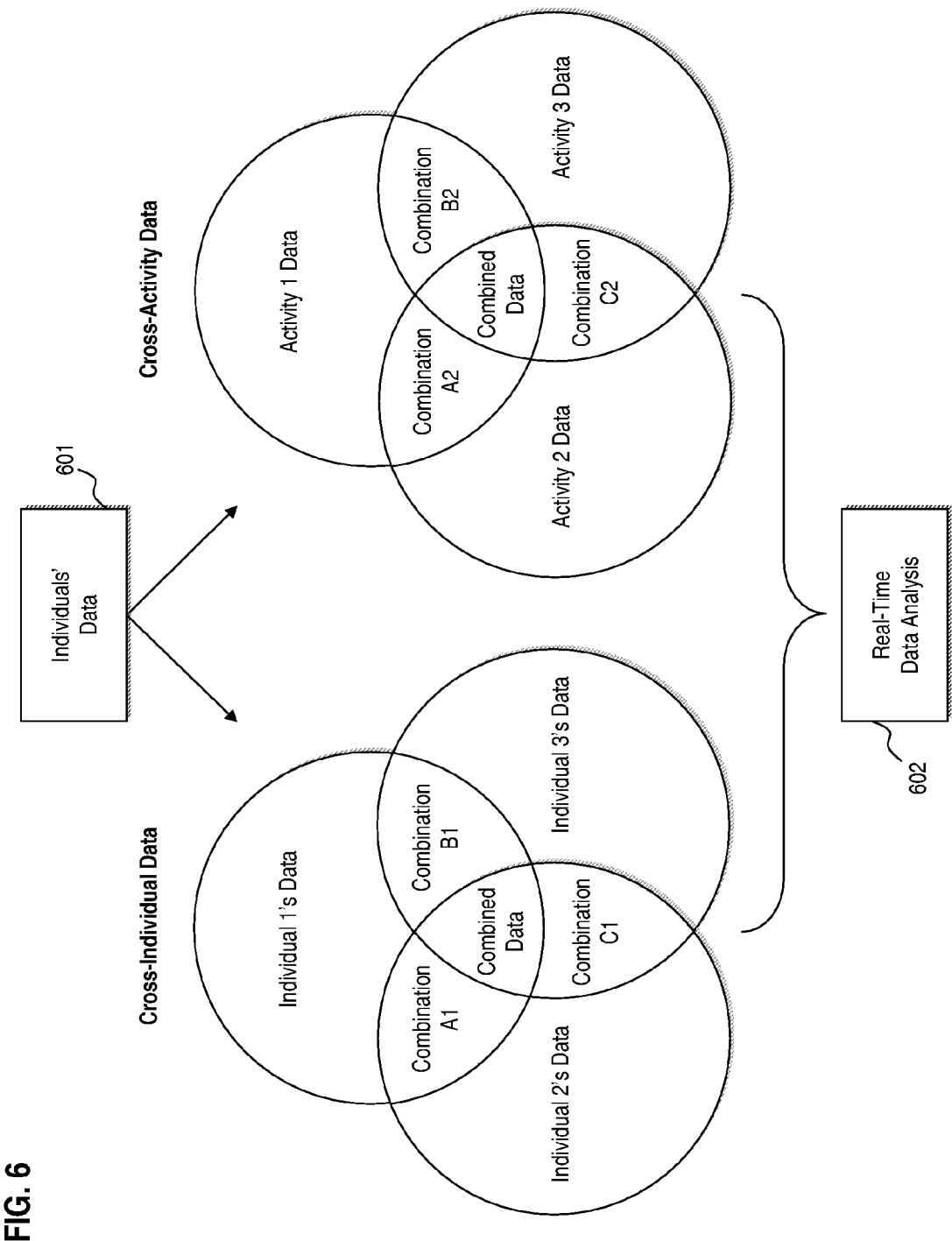
FIG. 6 depicts various combinations of user data for real-time data analysis, in accordance with an embodiment of the present invention.

Referring to FIG. 6, depicted are various combinations of individuals' data 601 for real-time data analysis, using component 602, in accordance with an embodiment of the present invention. DAS 200 can perform cross-individual data analyses on any commonly stored statistic. Accordingly, data will be segregated among individuals, e.g., individuals 1, 2, 3, according to the one or more chosen statistics. These individuals might represent team members in an EBG league, group members from a GAA group, randomly selected users, lone individuals, or all individuals of the system. Further, a user can request cross-individual analyses among any set of the possible individuals, e.g., individuals 1, 2, or 3, combination A1, B1 or B2, and combined data sets for every DTA participant. Moreover, while only three individuals' data are depicted, those skilled in the art will appreciate that any number of users' data may be combined for analysis.

Likewise, DAS 200 can perform cross-activity data analyses using the normalized data described above. In this manner, data can be segregated among activities, e.g., activities 1, 2, and/or 3, and according to a chosen statistic stored in conjunction with that particular activity. Further, cross-activity analyses may be among any set of the possible activities, e.g., activity 1, 2, or 3, combination A2, B2, or C2, and combined data sets for every league activity. Moreover, while only three activities' data are depicted, those skilled in the art will appreciate that any number of activities may be combined for analysis.

As an example of the types of analyses the DAS 200 can perform, a user might be interested in activities associated with martial arts training, cardiovascular work and weight training. As such, the user can request data analysis, at system 602, on these activities to examine the proportion of time spent across each activity and an associated level of soreness felt after working out. In this regard, the user could use this type of analysis to understand the optimal proportion of activity to be spent in each activity prior to a competition. A user might also compare optimal proportions to that of other martial artists in the system using a cross-individual analysis. The user could utilize this information to forecast an expected level of performance for other participants in the upcoming competition. Further, the user might also compare activity performance to dietary regimes to learn what combinations of foods, calories, nutrients, etc. contribute best to overall athletic development.

Additionally, those of ordinary skill in the art should appreciate that each of the DTA, EBG, GAA, DAS and QCD subsystems can interact with one another. For example, GAA functionality might be incorporated into EBG leagues or the EGB subsystem might utilize analysis produced by DAS. As such, it should be understood that the various subsystems of the fitness analysis system can be provided in a distributed environment or incorporated as a centralized unity.

Referring back to FIGS. 1 and 2, the fitness analysis system 111 can also provide a host of services related to data collection and/or analysis. One of these services can be a downloadable printout sheet with user planned activities on it. In this manner, the sheet will designate fields for the user to record statistical data. After performing the planned activities, the user could fill in those fields with the appropriate data and fax, email, or otherwise transmit the information on the sheet back to the fitness analysis system 111 for entry into the database.

Another service might allow for data maintenance of organized sporting and activity leagues. In such an embodiment of the present invention, an individual's data could be entered and/or edited by certain other individuals with special permission to access the data like coaches, parents, teachers, league commissioners, etc. The data could be maintained for the various statistical measures relating to the league being tracked. As an example, the present invention could be used to track a little league baseball season. The league commissioner could store data on players, teams, conferences, rankings, coaches, referees, at bats, strike outs, innings, homeruns, etc.

Yet another service of the present invention allows for verification of completed activities. In this manner, fitness analysis system 111 can provide a level of accreditation or validity to the user entered data for a particular activity. For instance, a user might enter that he/she ran 100 miles but only burned five calories or only took 30 minutes. The system 111 could flag these data fields for confirmation by another individual such as a health facility or through computer analysis. Further, the fitness analysis system 111 can be used to register individuals to participate in events such as non-profit marathons, community service activities, etc.

Still a further service the fitness analysis system 111 can provide is an overall system of records and achievements much like the records component within the EBG subsystem 204. In this embodiment, however, a form of "world records" can be established across all individuals using the system. Accordingly, participants who possess the best statistical performance in each recorded vital and activity statistic and/or calculated data field could receive recognition for their performance. As described earlier, this recognition could take the form of a textual bracket, a standings list, a graphic trophy, or other like method.

The system 111 can also be used to monitor physical injuries, symptoms, severity, causes, etc. This data can be correlated against the vast data store of individual entries to create relationships between various injuries and activities that cause them. By combining diet and nutritional data into each of the services described above, the fitness analysis system 111 can track individuals' overall health, establish warnings for risky behaviors or habits, suggest diets, exercise plans, etc. The system 111 can also alert individuals that they are overtraining, overexerting, or not exercising enough. Users can also establish alert parameters within the fitness analysis system such that if a defined parameter is satisfied, the system would automatically notify the user of such an occurrence.

Still another service the fitness analysis system 111 can perform is a mapping system that informs individuals where they can participate in certain activities for various geographic locales. For example, the fitness analysis system 111 can list fields where baseball can be played, or cycling routes that have mile markings. Maps of these areas can be provided along with generalized driving or walking directions.

As explained earlier, the present invention can communicate with one or more third party web servers, or equivalent online systems, via network. FIG. 7A illustrates such a scenario wherein a third party blog implements functionality provided by present invention. In this manner, the present invention is remotely embedded into, linked with and/or pushed to the third party blog using known methods. Such methods might include plug-in modules, provided code, linked fields, pushed applications, etc.

As seen in FIG. 7A, a blog interface 700 (e.g., "Bob's Blog") can provide users access to real time data analysis, provide subsets of information relating to performed and scheduled activities, league standings and statistics, goal status, and the like. The third party blog 700 could also be a forum for displaying record achievements 701 such as the fastest mile run. Additionally, the third party blog could provide audio links within presentations 1 and 2 in 701 and 702 respectively to the above described information or archival links 702 to additional data presentation.

Figure 7B:
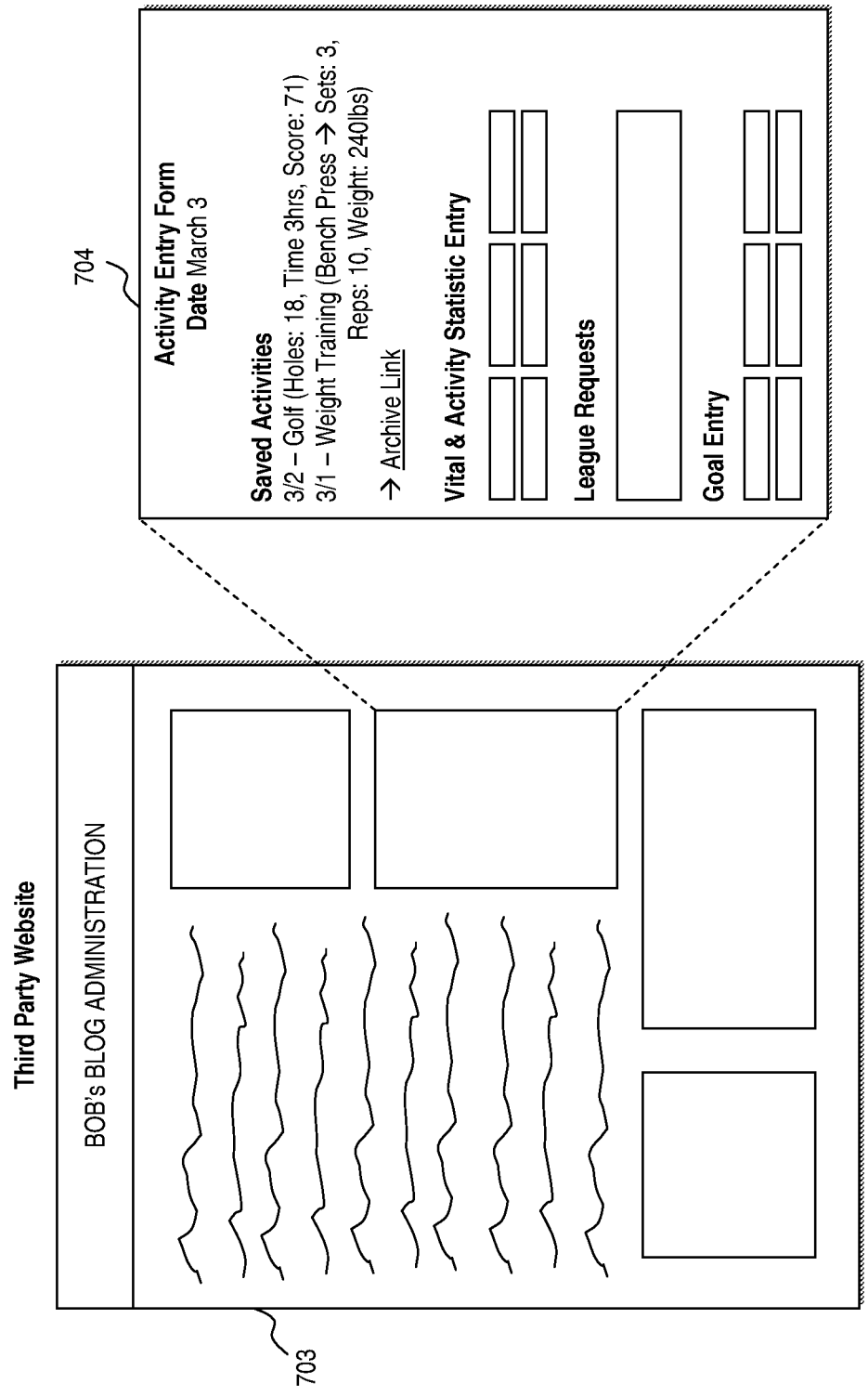

FIG. 7B illustrates a third party blog administration site 703 implementing additional embodiments of the present invention. As shown, blog administrators and/or visitors with permission could have access to an online data entry form 704 to write, edit, or otherwise modify vital and activity statistics for transmission to the fitness analysis system. In the depicted embodiment, the online form might include previously saved activities, an archival link to additional activity information, and/or establish fields for vital and activity statistic entry, league requests, or goal entry.

While described with respect to a third party blog implementing select embodiments of the present invention, those skilled in the art would appreciate that any subsystem or subcomponent of the present invention can be remotely embedded into, linked with and/or pushed to any type of third party content management system, web site, web server, or other online system.

Figure 8A:
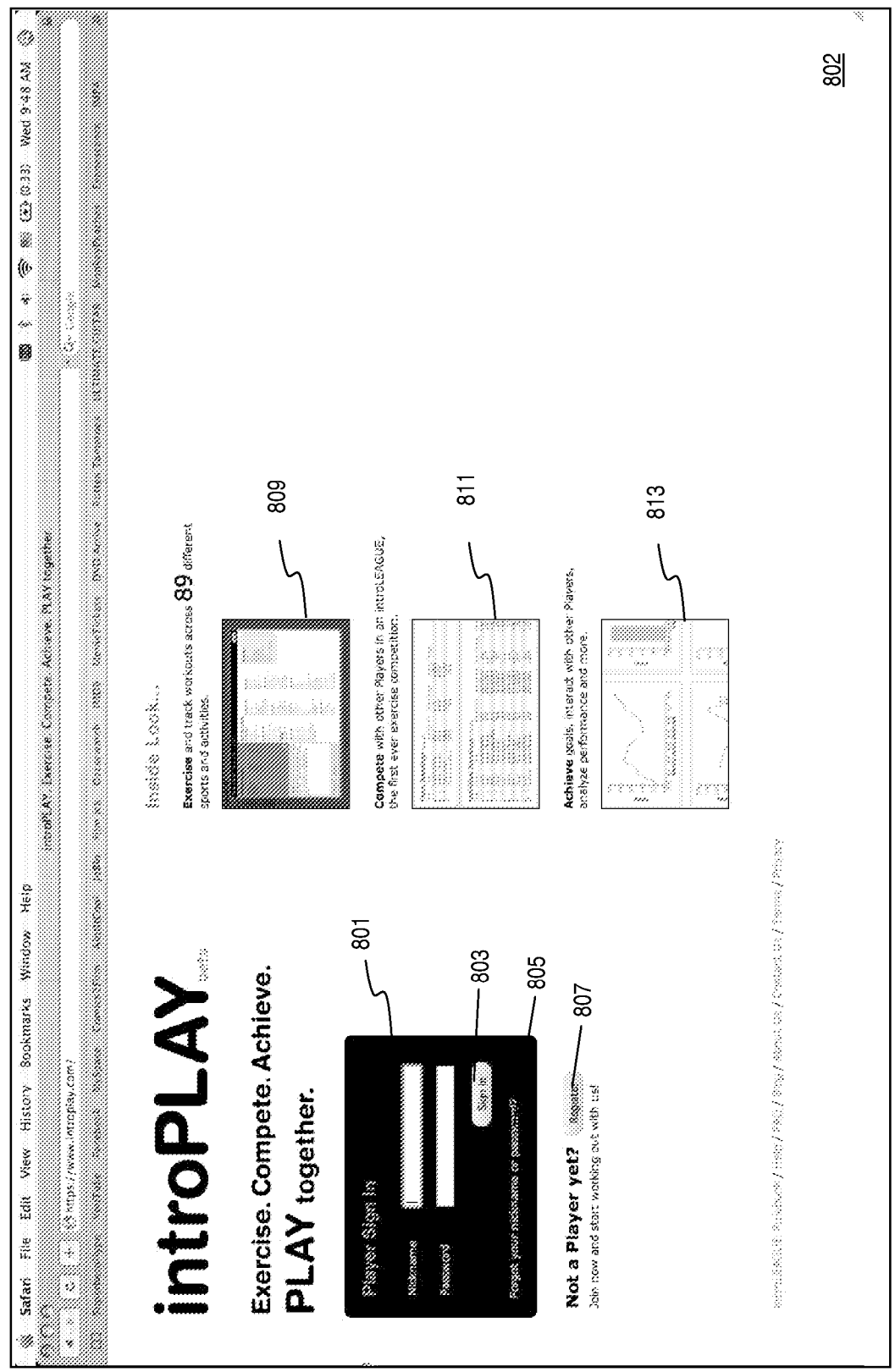
FIGS. 8A-8T depict exemplary graphical user interfaces (GUIs) providing tracking and analysis of fitness activities, according to various embodiments of the present invention.
Figure 8B:
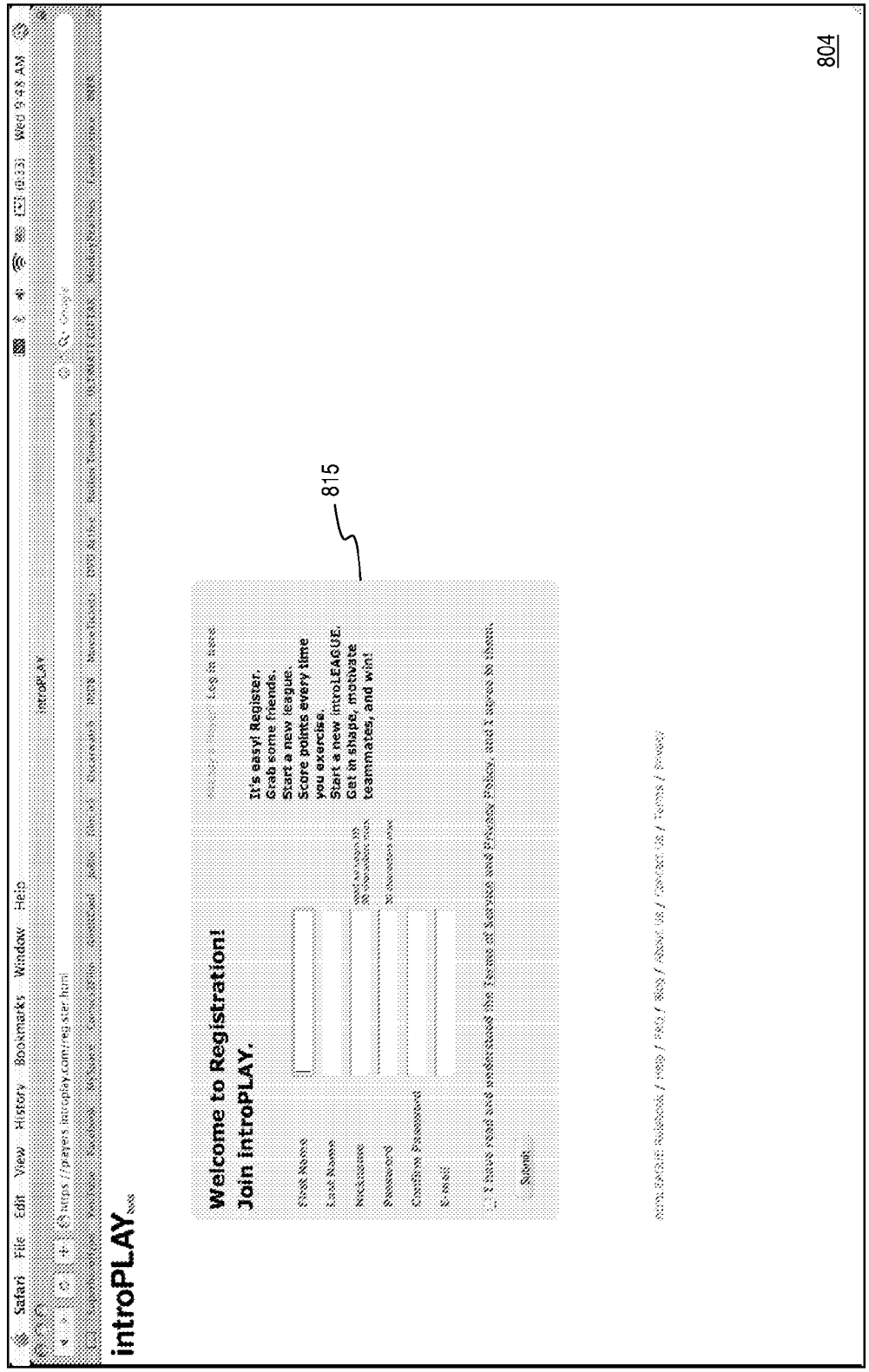
Figure 8C:
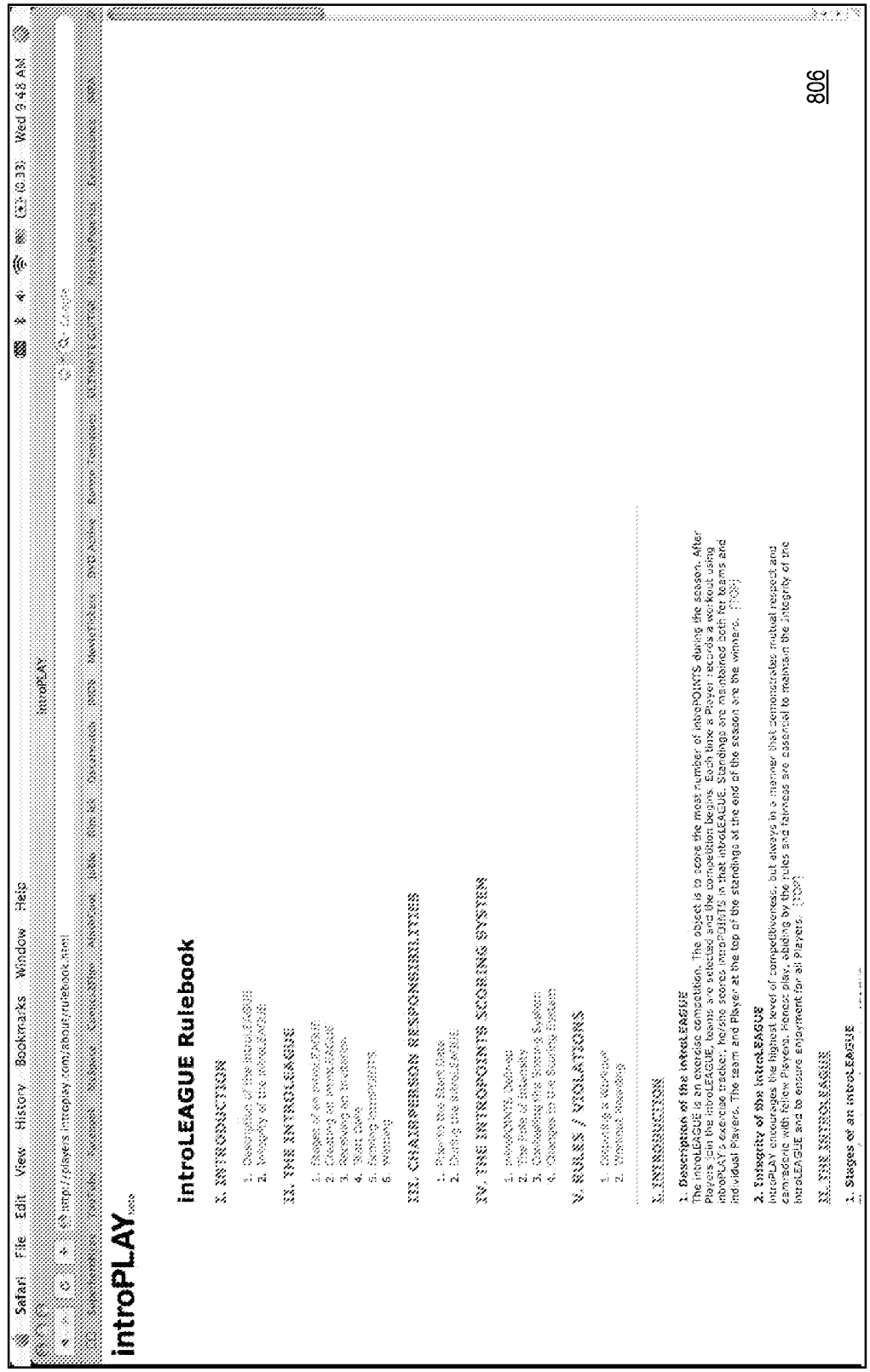
Figure 8D:
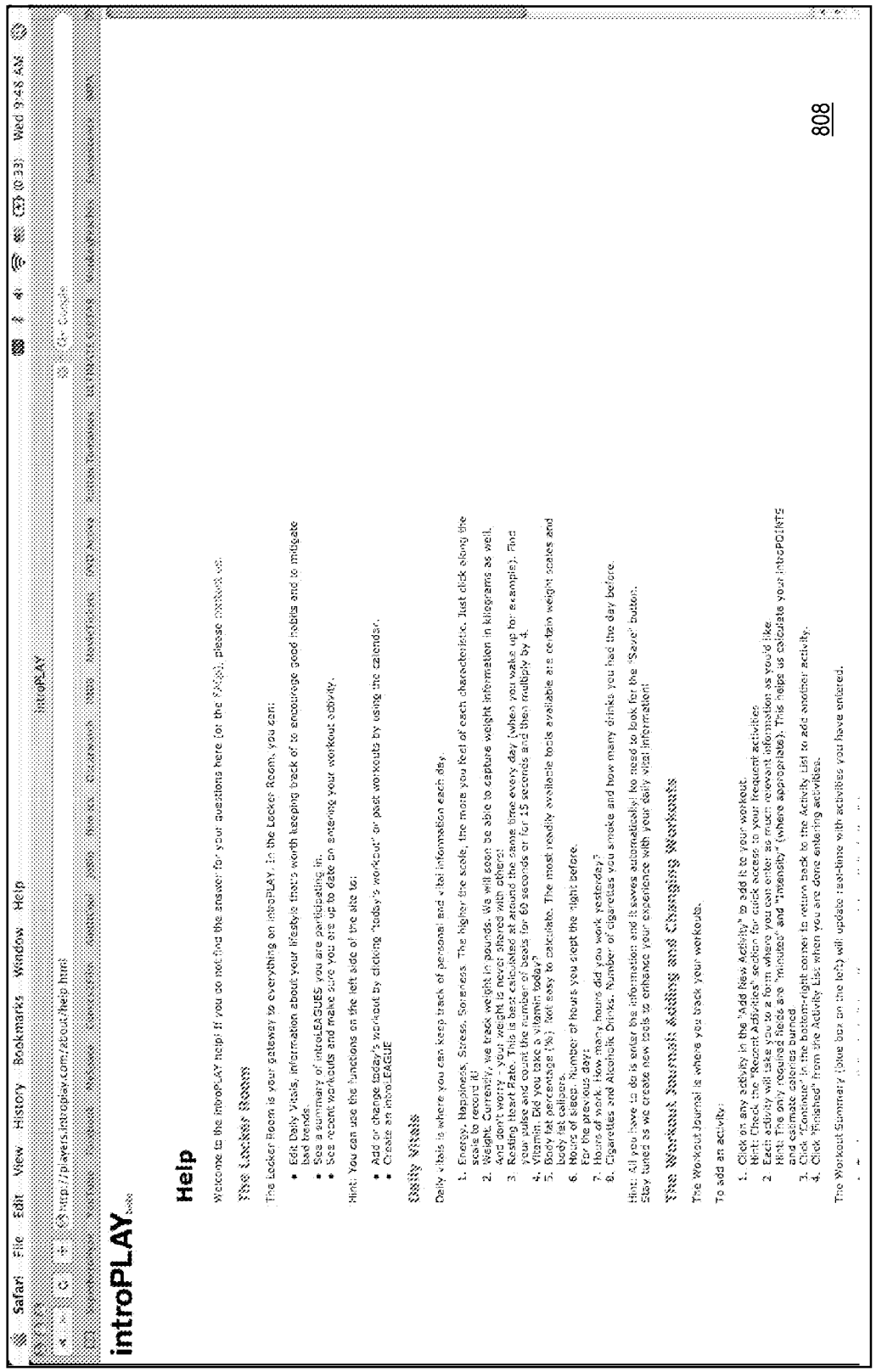
Figure 8E:
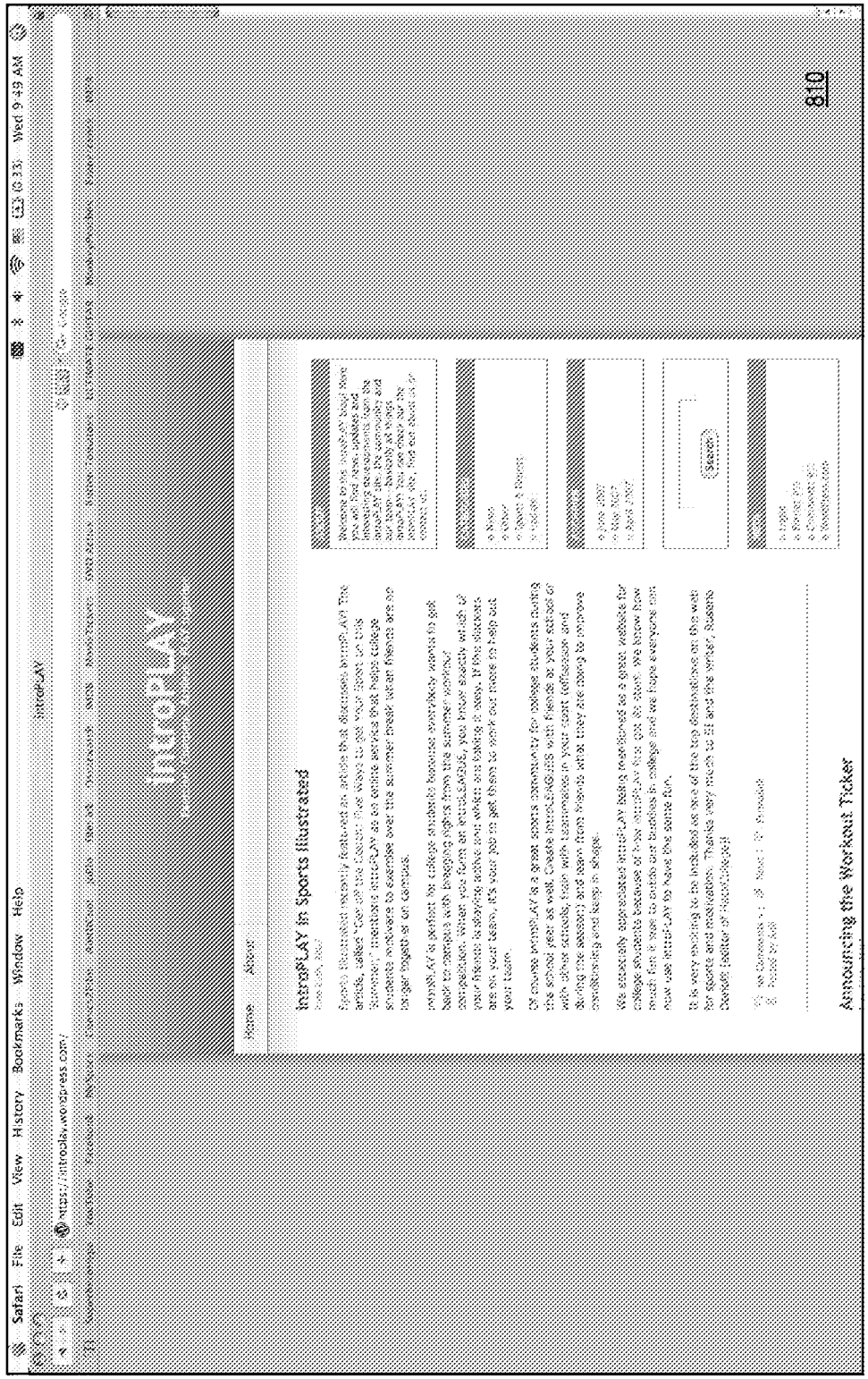
Figure 8F:
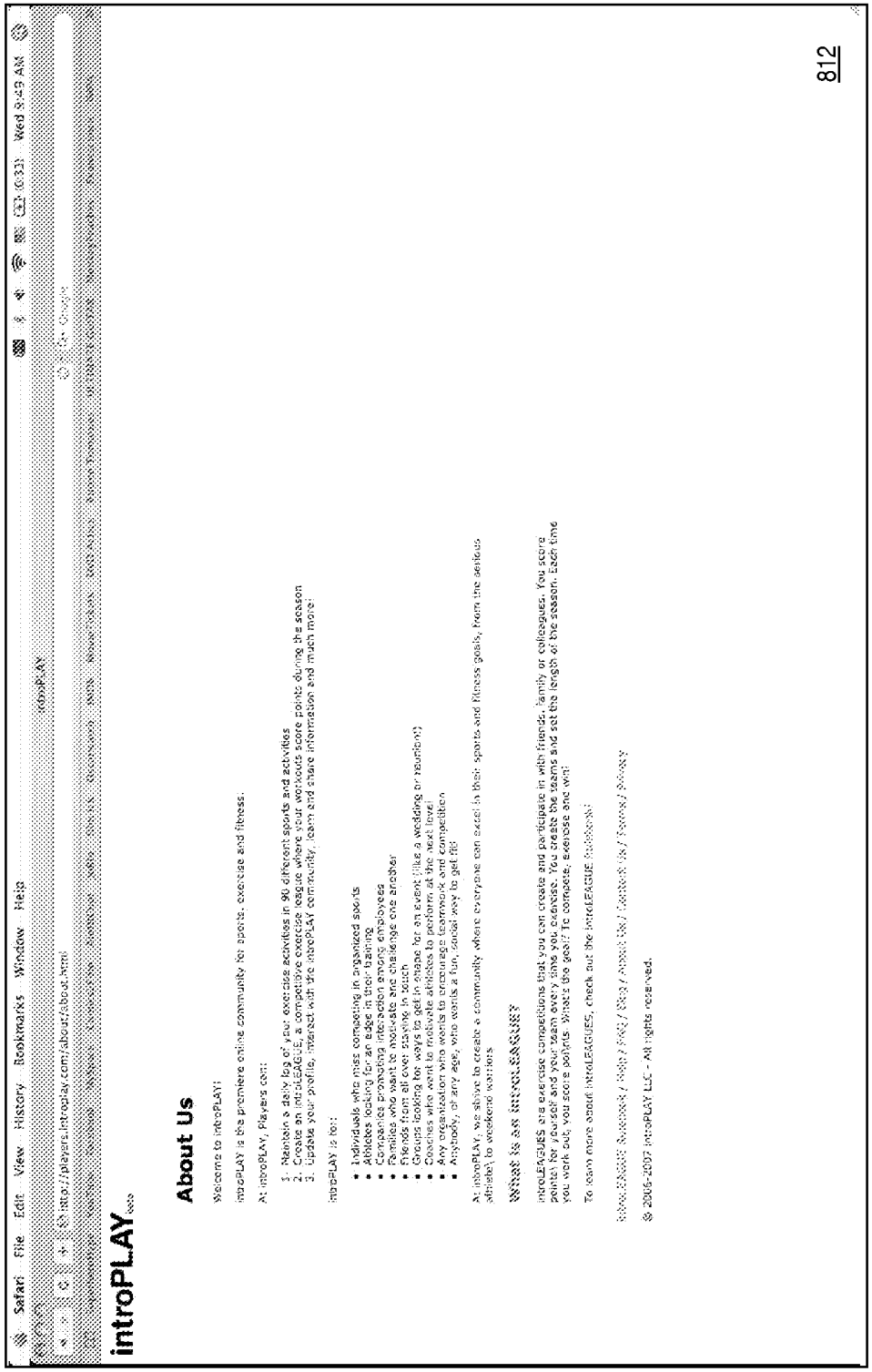
Figure 8G:
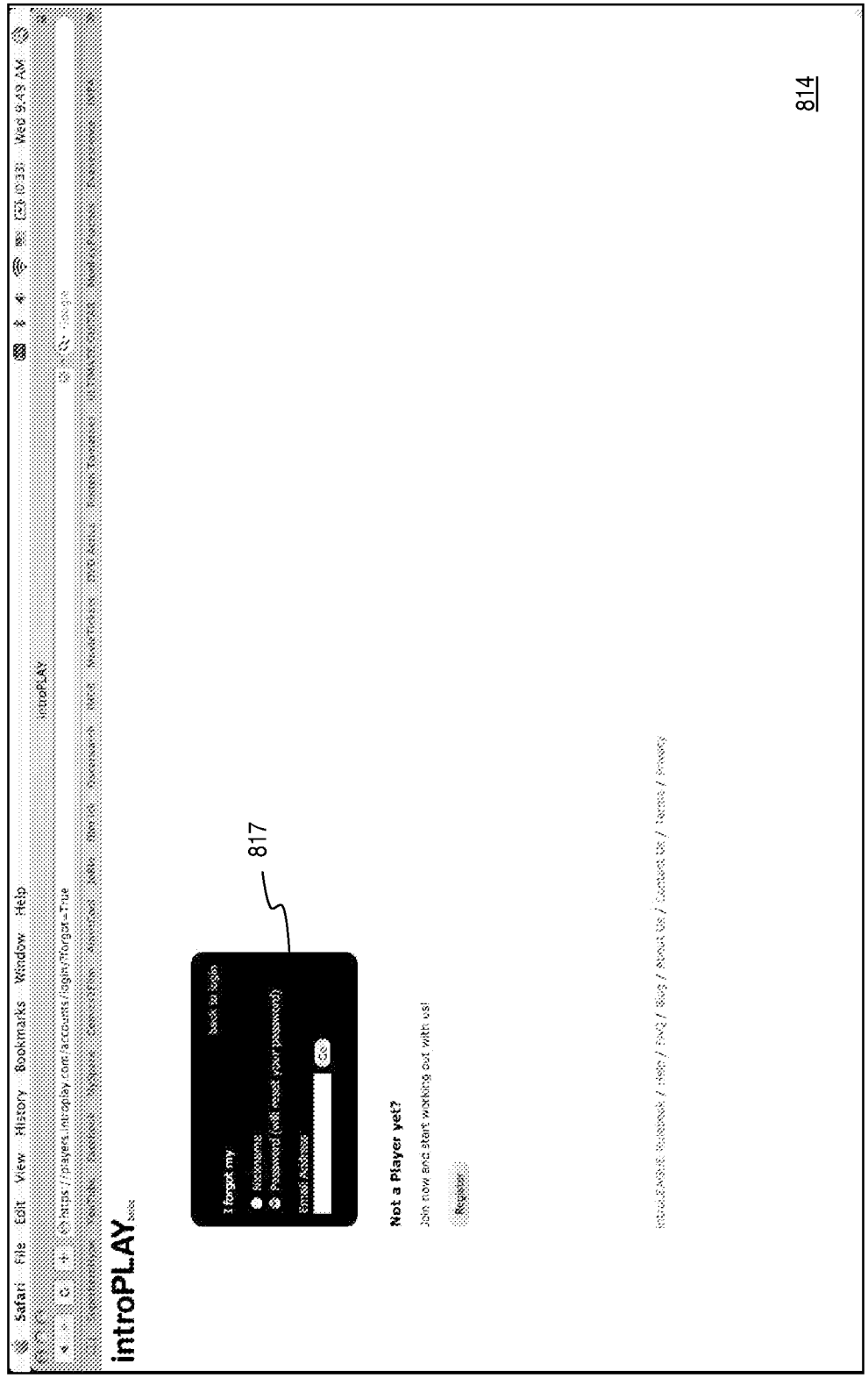
Figure 8H:
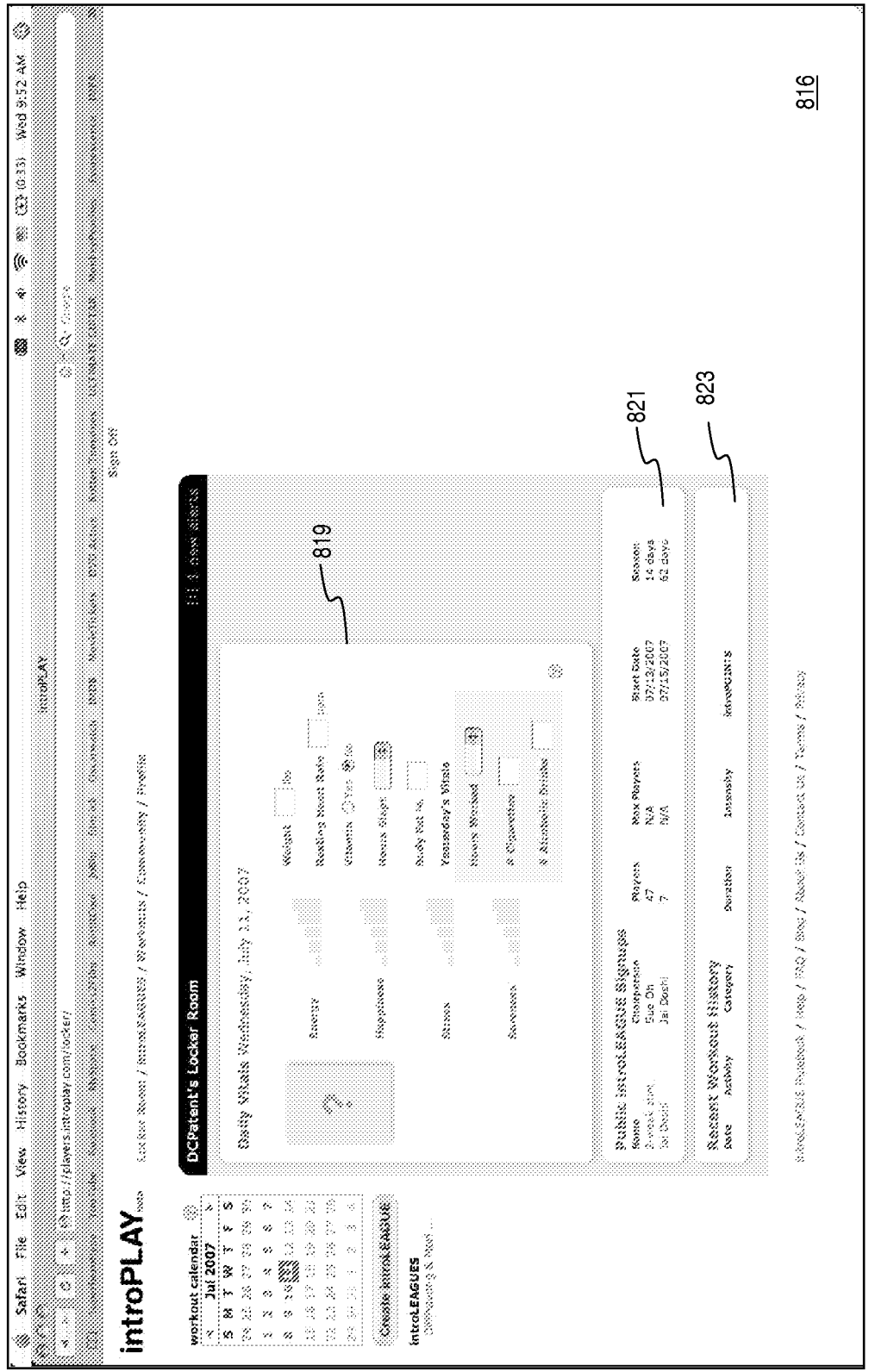
Figure 8I:
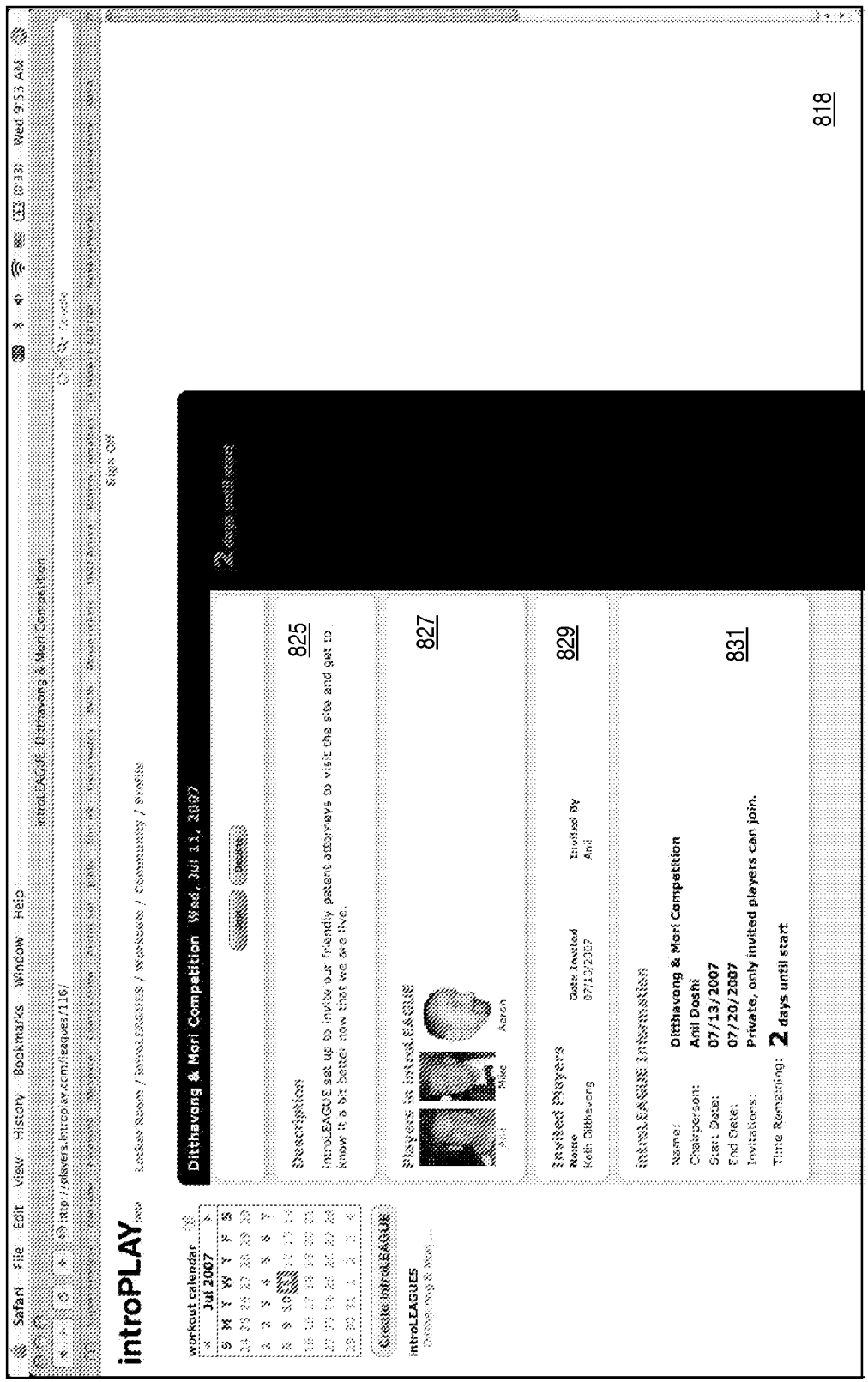
Figure 8J:
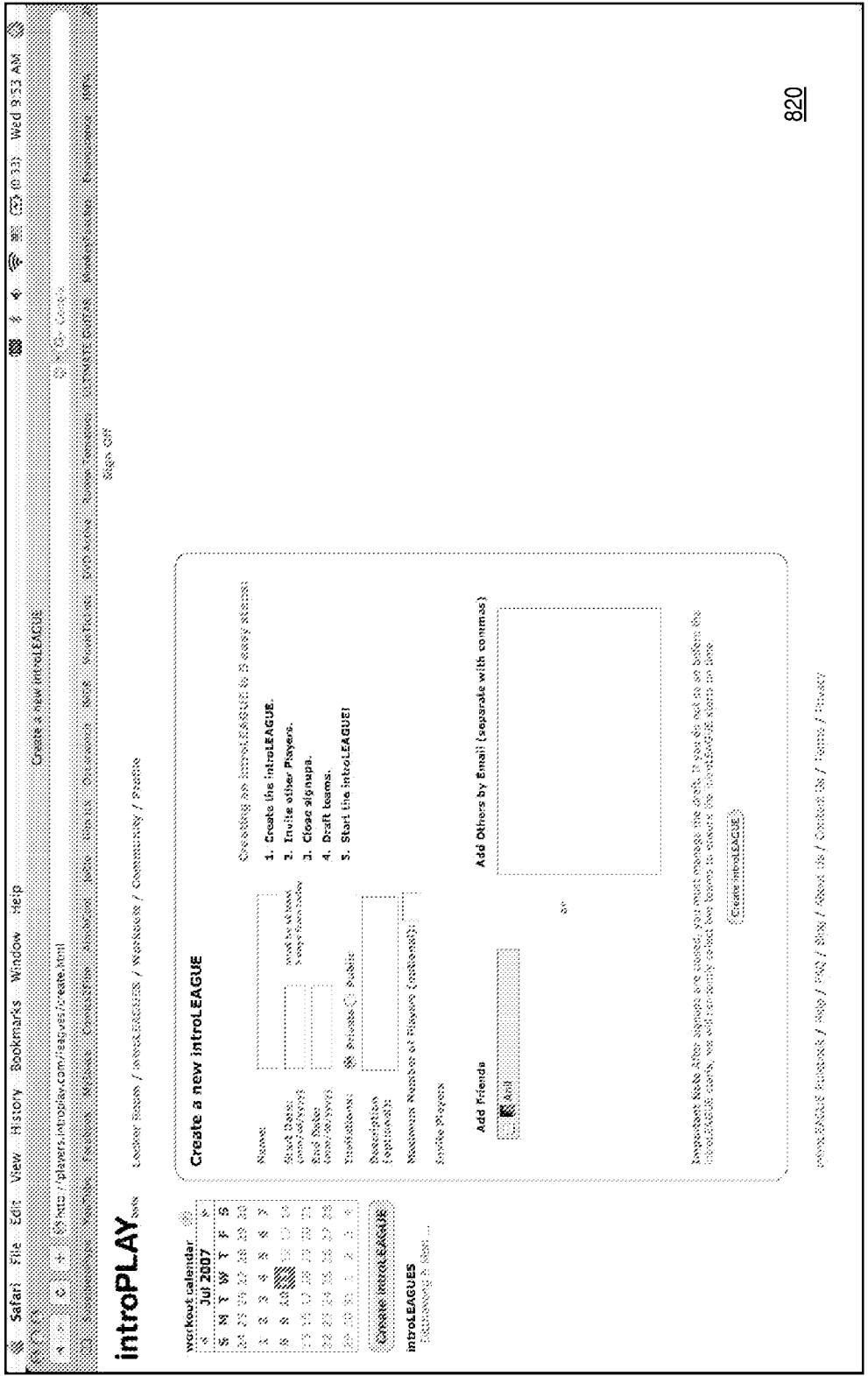
Figure 8K:
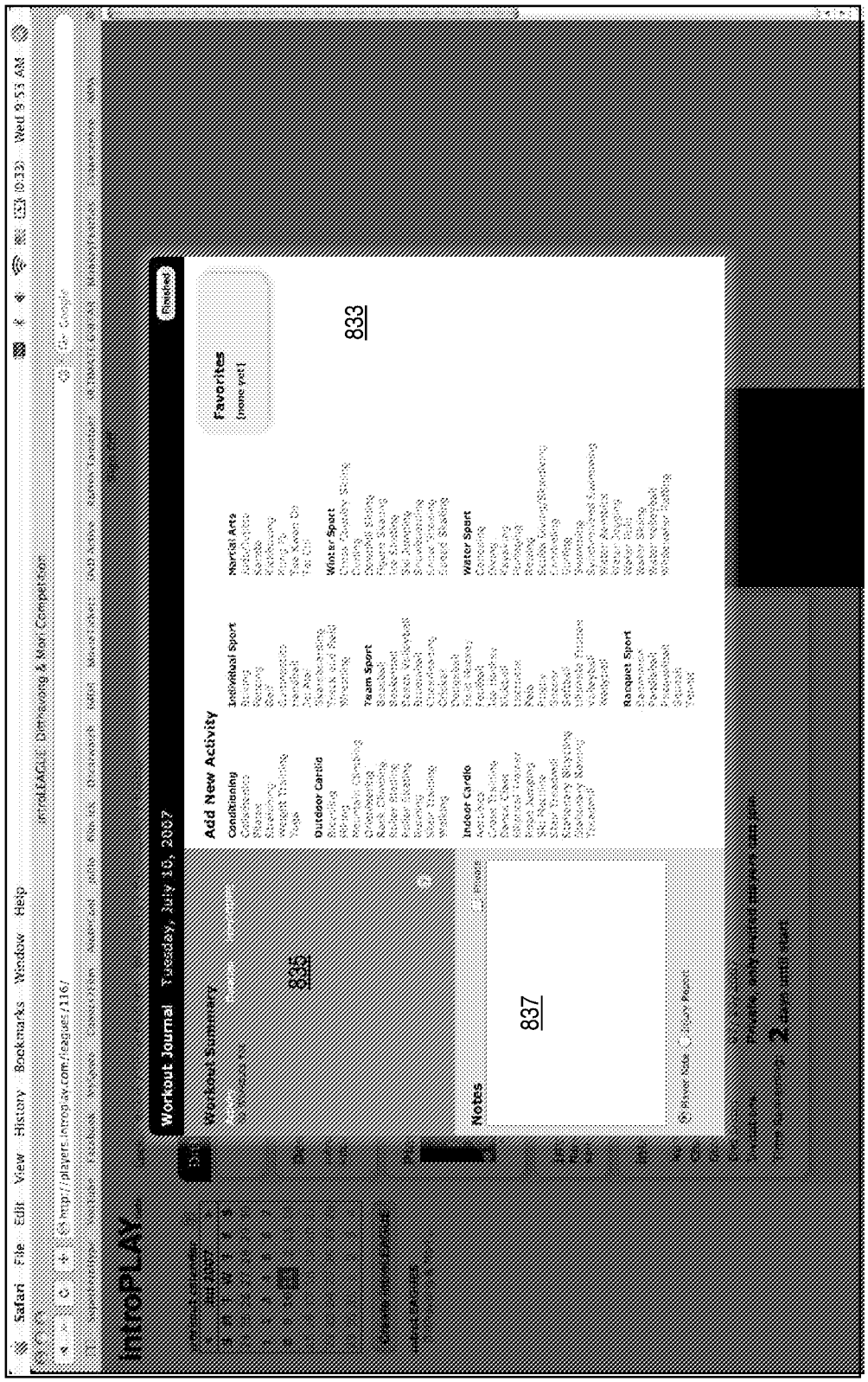
Figure 8L:
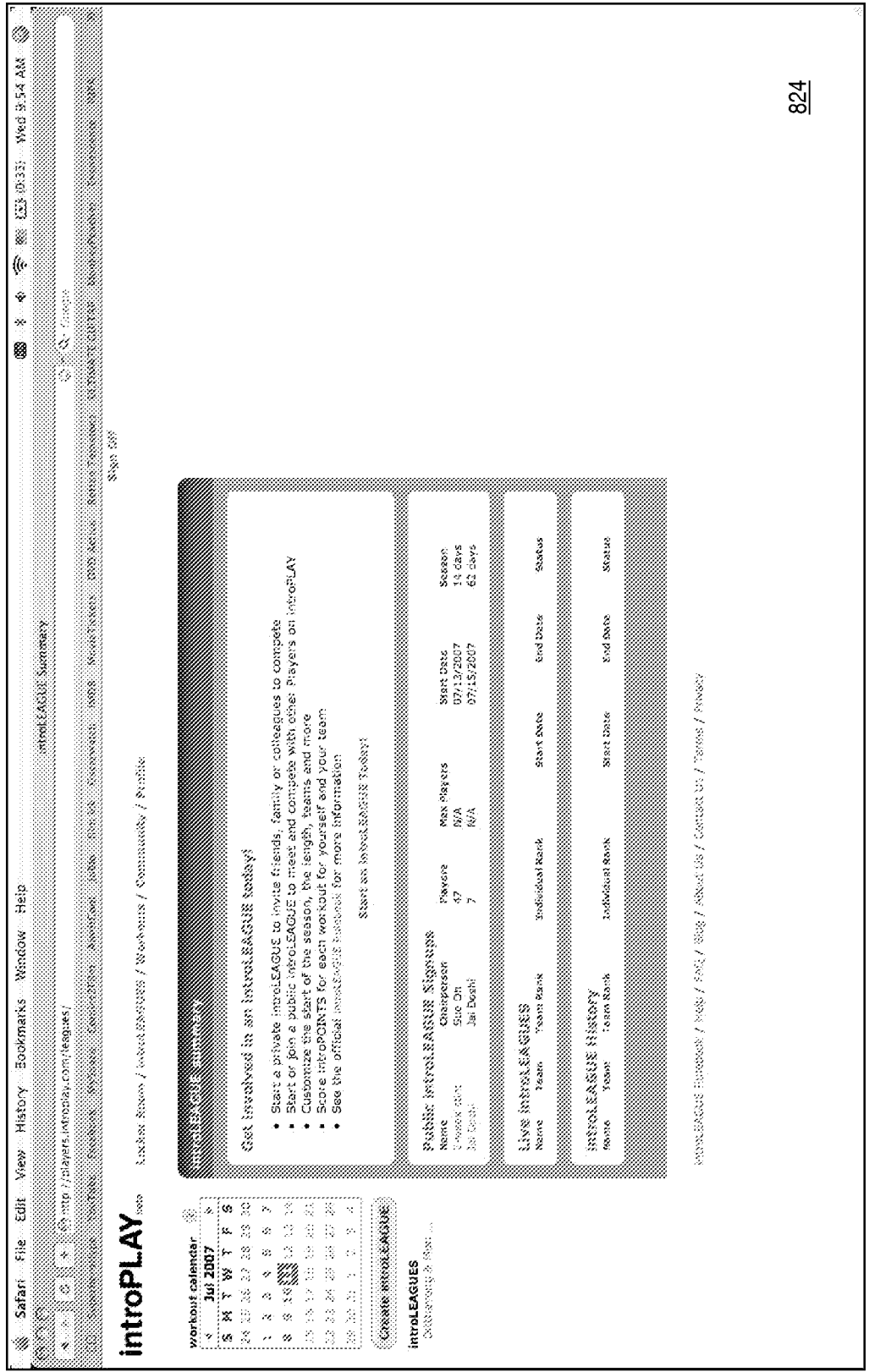
Figure 8M:
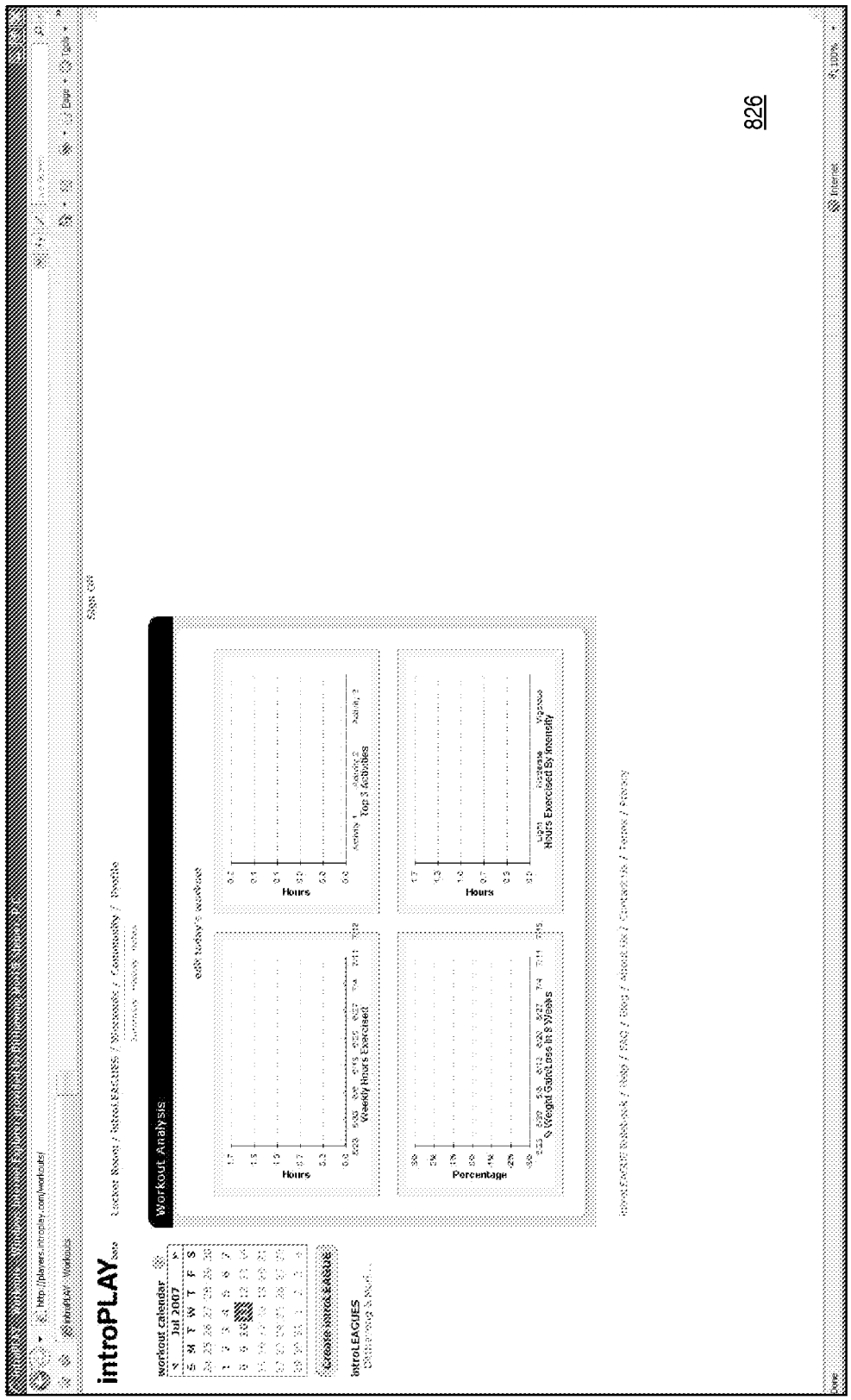
Figure 8N:
Figure 80:
Figure 8Q:
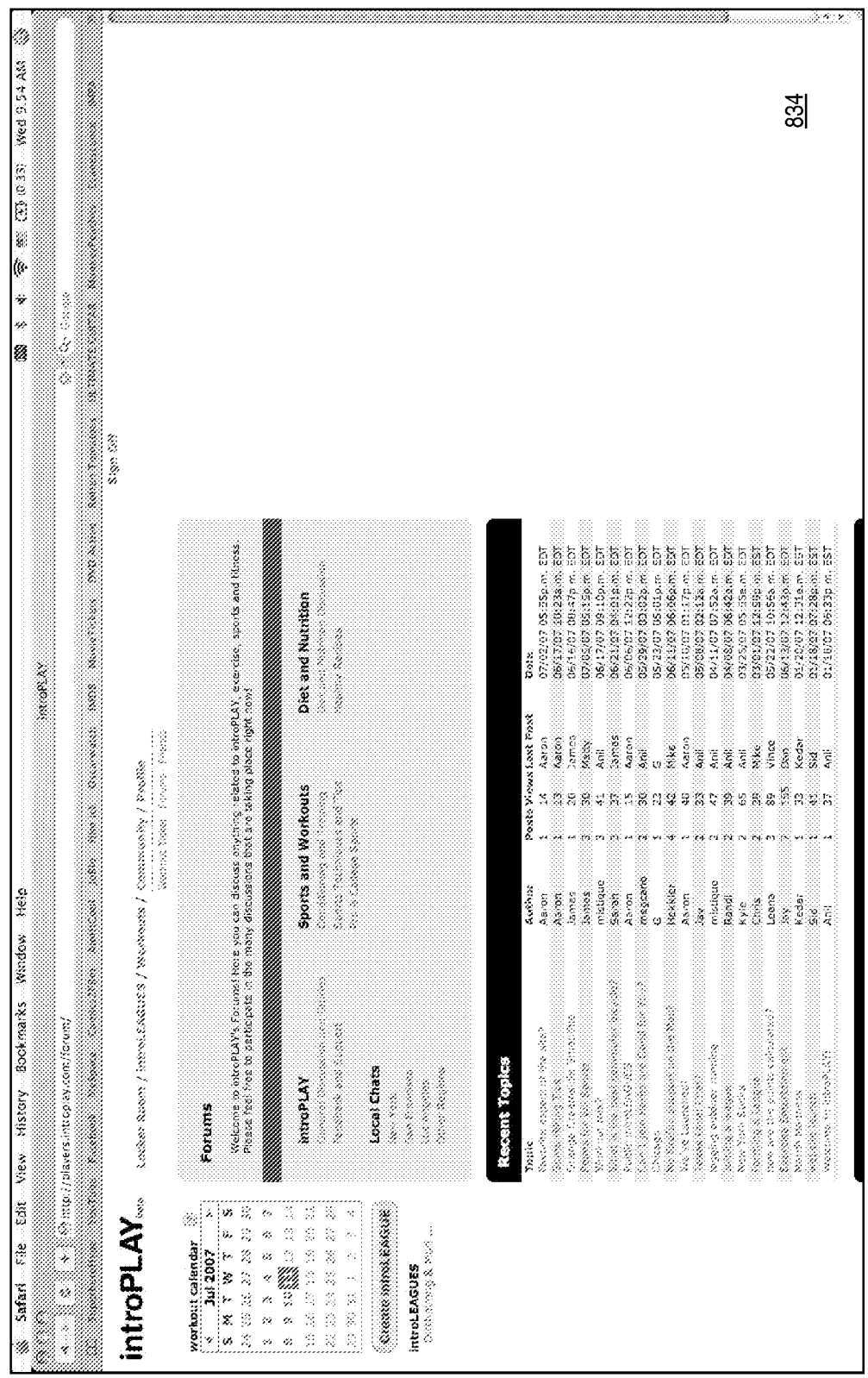
Figure 8R:
Figure 8S:
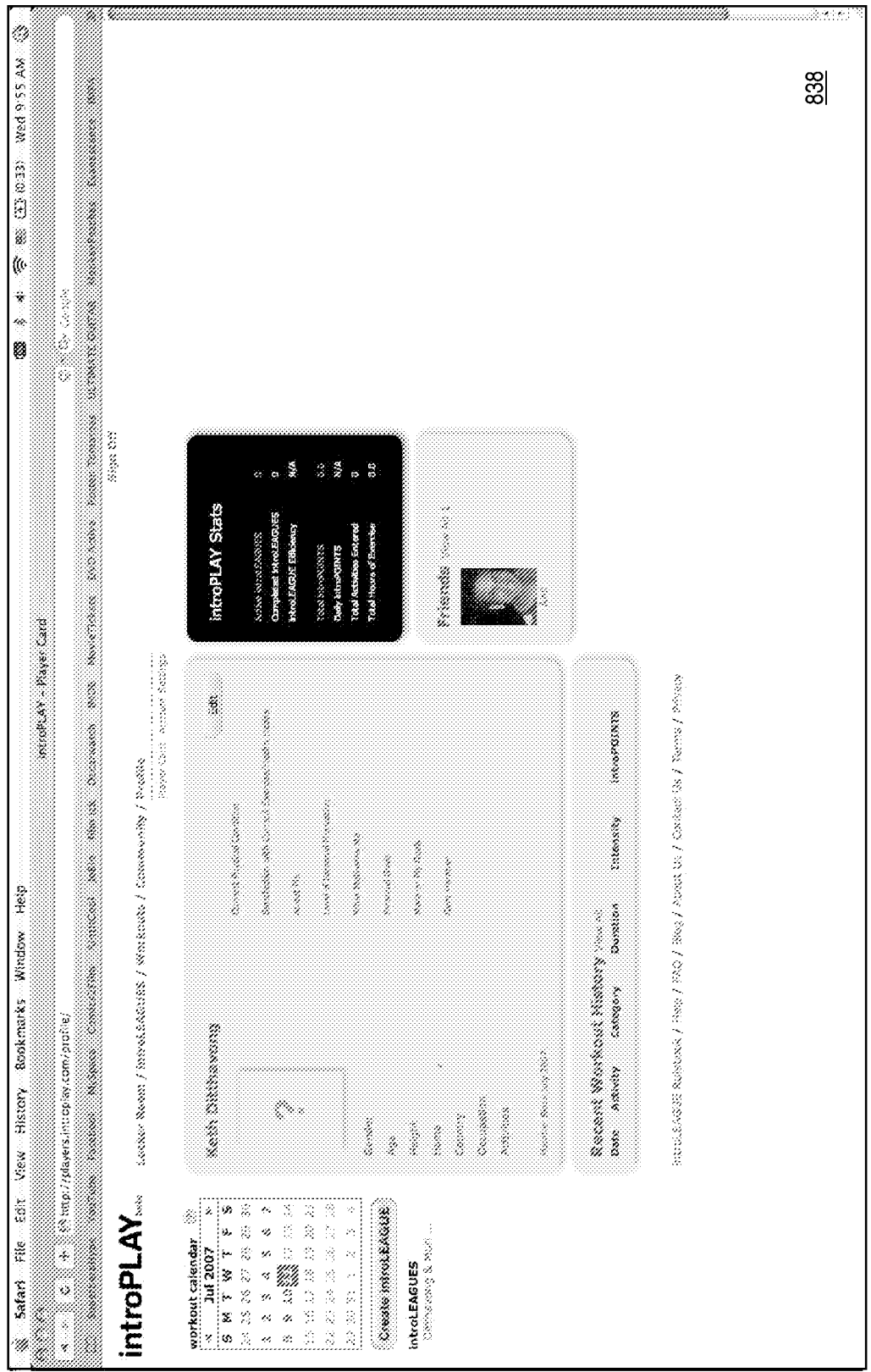
Figure 8T:
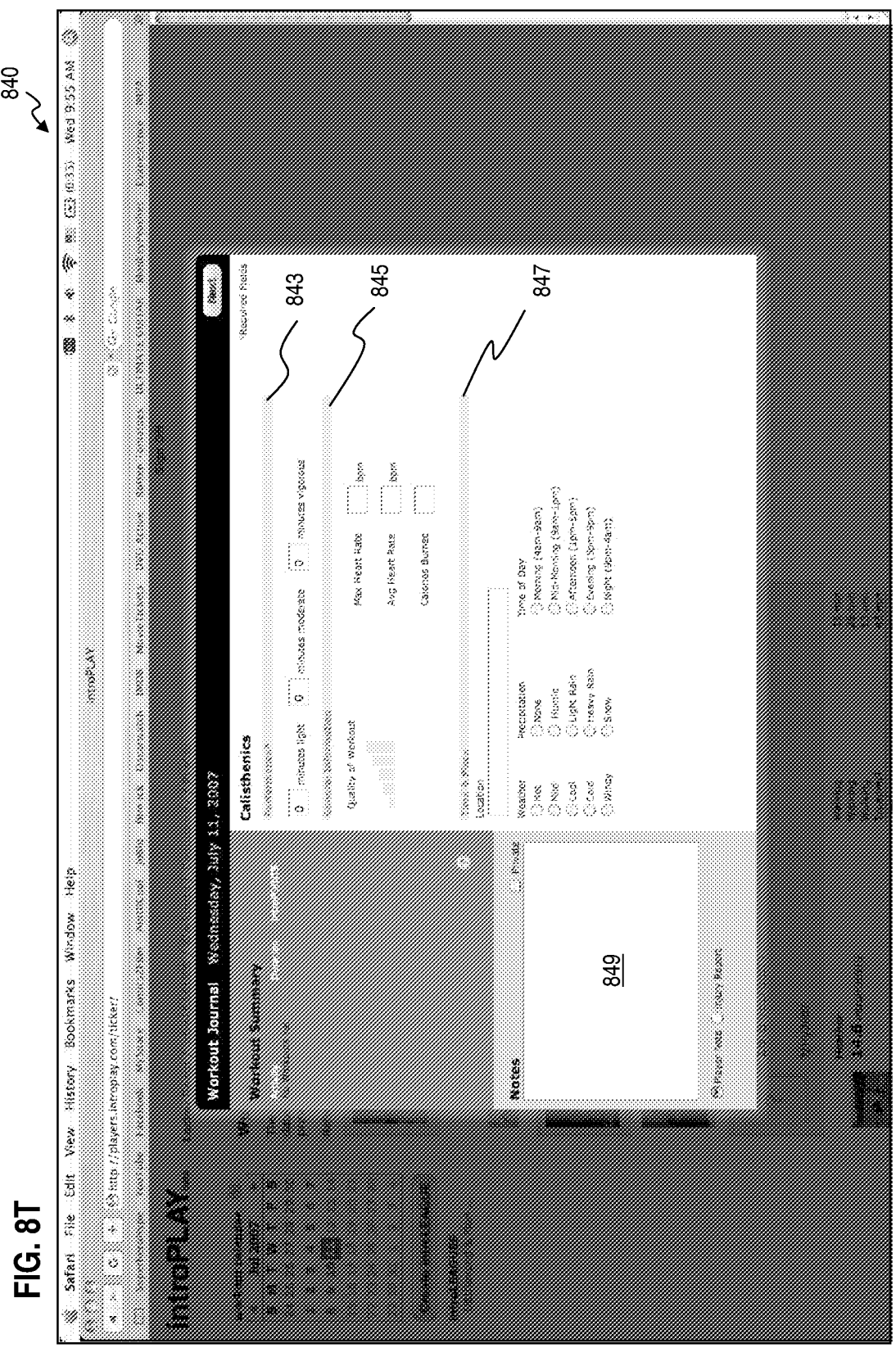

FIGS. 8A-8T depict exemplary Graphical User Interfaces (GUIs) according to various embodiments of the present invention.

FIG. 8A is an exemplary GUI 802 depicting a Main Home Page for a website employing the present invention. Registered members wishing to return to the website are asked to sign in at 801 using their nickname and password, for example. In an exemplary embodiment, the nickname may be an e-mail address, a name the member gives himself/herself for this account, or any other type of user identification the system and/or the member agree to use to identify the member. In typical fashion, after entering the nickname and password, the member clicks on "Sign In" at 803 to enter the website. Should the registered member forget his/her nickname and/or password, the member may click on "Forgot your nickname or password" at 805 and be directed, in known manner, to a site where personal information may be requested to ensure that the member is indeed that member and the nickname/password will be supplied to him/her in a known manner, e.g., by sending the information to a registered e-mail address for that member. New, or unregistered, users are given the opportunity to sign up by activating the "Register" button at 807, which directs them to a site for entering all relevant information in a known manner, as depicted in FIG. 8B. New users are also given the opportunity to preview thumbnails of some of the website's features, e.g., exercise and track workouts thumbnail at 809, compete with other players thumbnail at 811, and achieve goals, interact with other players thumbnail at 813.

FIG. 8B is an exemplary GUI depicting a registration page 804 where new users may sign up to be members. The new user would enter all required information into block 815, including a first and last name, a member username, or nickname, by which the member would like to be identified on the website, a password allowing entrance to the account, and an e-mail address. The user must then agree to the terms of use and conditions, by checking the appropriate box at the bottom of block 815, in order to complete registration.

FIG. 8C is an exemplary GUI 806 depicting a page of a league rulebook While the rulebook comprises a plurality of pages, the figure illustrates just one page of the rulebook which displays and discusses many of the website's features, including the concepts and standards of operation.

FIG. 8D is an exemplary GUI 808 depicting an exemplary Help page which provides insights on the various sections of the website, employing explanatory text to aid users in navigating and using the different areas of the website, such as The Locker Room feature depicted in GUI 808.

FIG. 8E is an exemplary GUI 810 depicting the Blog feature of the website. This feature is best described as an online journal edited by Administrators of the website. The Blog may contain, for example, news about the website and its operation and newly added features that the Administrators may wish to share with users of the website. As shown in the example of FIG. 8E, the Administrators share relevant a news article.

FIG. 8F is an exemplary GUI 812 depicting an About Us page of the website. On this page, users may find information relating to the objectives and purposes of the website, e.g., that users may maintain a daily log of exercise activities in 90 different sports and activities, or that users may learn about the leagues of the present invention.

FIG. 8G is an exemplary GUI 814 depicting a webpage to which the user is directed when activating the "Forgot your nickname or password" button 805 in FIG. 8A. The information block 817 of FIG. 8G permits the user to indicate whether it is the user's nickname or password that has been forgotten. Then, the user enters his/her e-mail address and activates the Go button to begin the process of retrieving the desired forgotten information.

FIG. 8H is an exemplary GUI 816 depicting the Main Locker Room page of the website. On this page, the user is permitted to enter his/her health statistics for that day in block

819. This page may also display current leagues, the number of players in each league and the length of time each league has been active in area 821. This page may also display the user's most recent workout history in area 823.

FIG. 8I is an exemplary GUI 818 depicting a league invitation page that can be used by users to either join a league or pass. In block portion 825, a description of the purpose may be given. In the example shown, the purpose of this league set up is to invite the patent attorneys handling the patent application to visit the website and get to know it a bit better. In block portion 827, a list of the current members of a team, along with photos of such members if desired and available, appears. Block portion 829 presents a list of members invited to join team. Block portion 831 presents other league information such as the name given to the competition, the name of the chairperson, the start and end dates of the competition and the type of invitation, e.g., "private, only invited players can join." There is also an indication on this page of how many days are left until the start time of the competition.

User members may also create a team as shown in the exemplary GUI 820 of FIG. 8J. A user establishes a new team by submitting the requested information into the appropriate portions of the screenshot. The required information includes a name for the new team and the start and end dates for the competition. Optionally, a user may choose to enter a description of the new team. This screen also provides the option of sending e-mails to invite others to join the team.

FIG. 8K is an exemplary GUI 822 depicting a webpage displaying various workout options, at block portion 833, and recent, or current workouts, along with numbers of points earned for a workout, at block portion 835. Also, at block portion 837, the user is given the option of providing notes.

FIG. 8L is an exemplary GUI 824 depicting a webpage a user may access for information about current teams that can be joined. This webpage may also display the history of teams of which the user has been a member.

FIG. 8M is an exemplary GUI 826 depicting a webpage that a user can access for graphical information regarding to the user's daily workout activity.

FIG. 8N is an exemplary GUI 828 depicting a webpage that a user can access whereby information regarding that user's workout history, along with the number of points earned, is displayed.

FIG. 8O is an exemplary GUI 830 depicting a webpage that a user can access in order to review any notes that user may have written (at block portion 839) or any injuries that may have occurred during workouts (at block portion 841).

FIG. 8P is an exemplary GUI 832 depicting a webpage that a user can access in order to view other users' most recent workouts and points earned. In this manner, the user is motivated to continue workouts in order to compete with other users in various activities.

FIG. 8Q is an exemplary GUI 834 depicting a webpage at which a discussion board may be accessed, permitting users to engage in discussion with other users regarding activities and other various topics of interest to the users.

FIG. 8R is an exemplary GUI 836 depicting an example of a thread of a discussion that may appear on the discussion board regarding specific topics.

FIG. 8S is an exemplary GUI 838 depicting a Main Profile Page. This webpage shows a user the user's personal information and statistics that a user may choose to share with other users.

FIG. 8T is an exemplary GUI 840 depicting a webpage relating to a workout journal that a user can access in order to review that user's workout summary in particular activities. The display block may show, in Performance block portion 843, the type of activity in which the user has engaged and the length of time the user engaged in that activity in a light, moderate, and vigorous manner. The display block may also show, in General Information block portion 845, the quality of the user's workout, by displaying the user's maximum heart rate, average heart rate, and the number of calories burned during the workout. Further, in Time and Place block portion 847, the user may view a record of the location of the workout and the weather conditions prevailing at that time, along with the time of day of the workout. The user may enter any desired notes in block portion 849.

Further, one of ordinary skill in the art would recognize that the processes for providing tracking physical activities and associated gaming may be implemented via software, hardware (e.g., general processor, Digital Signal Processing (DSP) chip, an Application Specific Integrated Circuit (ASIC), Field Programmable Gate Arrays (FPGAs), etc.), firmware, or a combination thereof. Such exemplary hardware for performing the described functions is detailed below.

Figure 9:
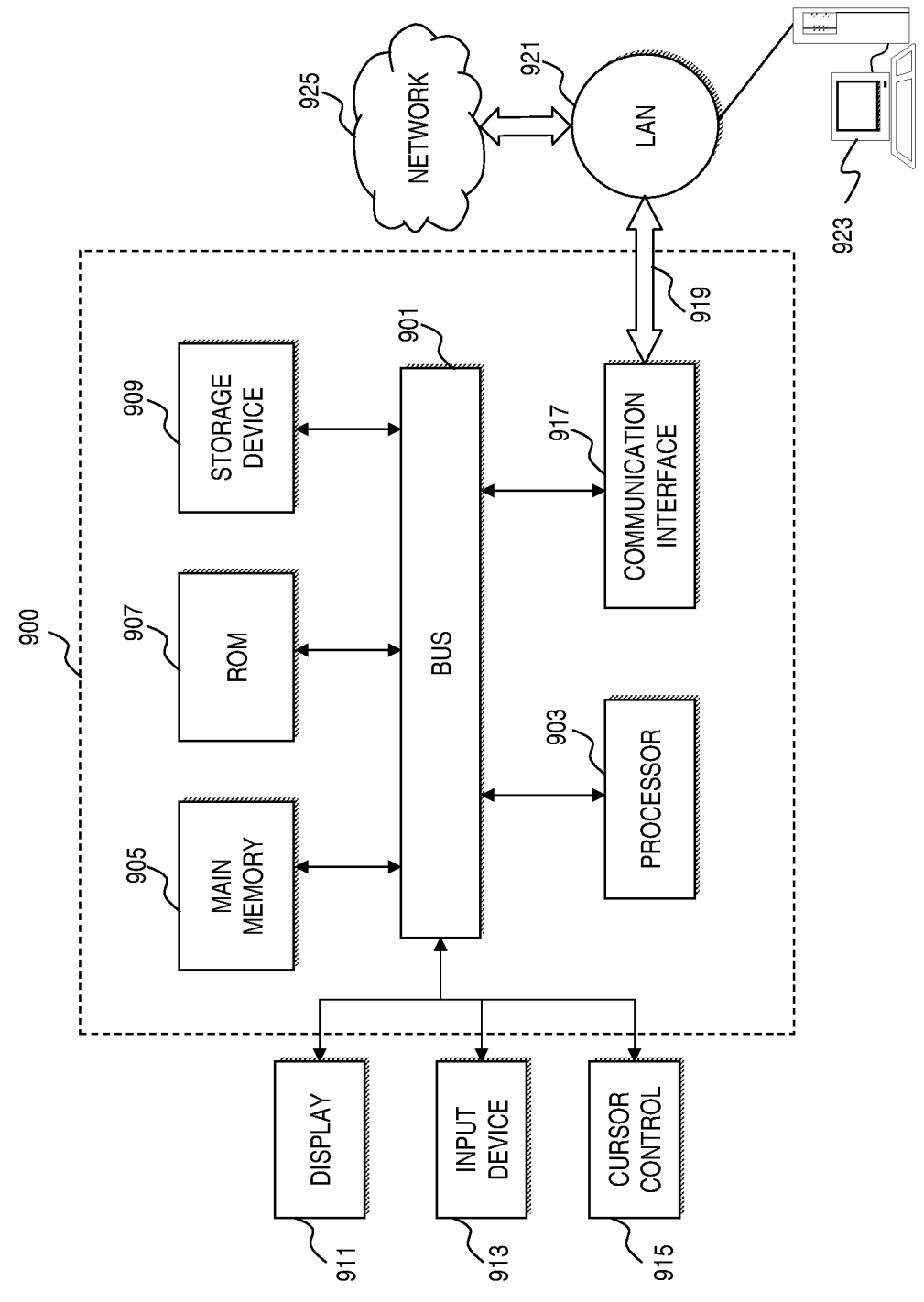
FIG. 9 depicts a computer system that can be used to implement an embodiment of the present invention.

FIG. 9 illustrates a computer system 900 upon which an embodiment according to the present invention can be implemented. The computer system 900 includes a bus 901 or other communication mechanism for communicating information and a processor 903 coupled to the bus 801 for processing information. The computer system 900 also includes main memory 905, such as a random access memory (RAM) or other dynamic storage device, coupled to the bus 901 for storing information and instructions to be executed by the processor 903. Main memory 905 can also be used for storing temporary variables or other intermediate information during execution of instructions by the processor 903. The computer system 900 may further include a read only memory (ROM) 907 or other static storage device coupled to the bus 901 for storing static information and instructions for the processor 903. A storage device 909, such as a magnetic disk or optical disk, is coupled to the bus 901 for persistently storing information and instructions.

The computer system 900 may be coupled via the bus 901 to a display 911, such as a cathode ray tube (CRT), liquid crystal display, active matrix display, or plasma display, for displaying information to a computer user. An input device 913, such as a keyboard including alphanumeric and other keys, is coupled to the bus 901 for communicating information and command selections to the processor 903. Another type of user input device is a cursor control 915, such as a mouse, a trackball, or cursor direction keys, for communicating direction information and command selections to the processor 903 and for controlling cursor movement on the display 911.

According to one embodiment of the invention, the fitness analysis system is provided by the computer system 900 in response to the processor 903 executing an arrangement of instructions contained in main memory 905. Such instructions can be read into main memory 905 from another computer-readable medium, such as the storage device 909. Execution of the arrangement of instructions contained in main memory 905 causes the processor 903 to perform the process steps described herein. One or more processors in a multi-processing arrangement may also be employed to execute the instructions contained in main memory 905. In alternative embodiments, hard-wired circuitry may be used in place of or in combination with software instructions to implement the embodiment of the present invention. In another example, reconfigurable hardware such as Field Programmable Gate Arrays (FPGAs) can be used, in which the functionality and connection topology of its logic gates are customizable at run-time, typically by programming memory look up tables. Thus, embodiments of the present invention are not limited to any specific combination of hardware circuitry and software.

The computer system 900 also includes a communication interface 917 coupled to bus 901. The communication interface 917 provides a two-way data communication coupling to a network link 919 connected to a local network 921. For example, the communication interface 917 may be a digital subscriber line (DSL) card or modem, an integrated services digital network (ISDN) card, a cable modem, a telephone modem, or any other communication interface to provide a data communication connection to a corresponding type of communication line. As another example, communication interface 917 may be a local area network (LAN) card (e.g. for Ethernet™ or an Asynchronous Transfer Model (ATM) network) to provide a data communication connection to a compatible LAN. Wireless links can also be implemented. In any such implementation, communication interface 917 sends and receives electrical, electromagnetic, or optical signals that carry digital data streams representing various types of information. Further, the communication interface 917 can include peripheral interface devices, such as a Universal Serial Bus (USB) interface, a PCMCIA (Personal Computer Memory Card International Association) interface, etc. Although a single communication interface 917 is depicted in FIG. 9, multiple communication interfaces can also be employed.

The network link 919 typically provides data communication through one or more networks to other data devices. For example, the network link 919 may provide a connection through local network 921 to a host computer 923, which has connectivity to a network 925 (e.g. a wide area network (WAN) or the global packet data communication network now commonly referred to as the "Internet") or to data equipment operated by a service provider. The local network 921 and the network 925 both use electrical, electromagnetic, or optical signals to convey information and instructions. The signals through the various networks and the signals on the network link 919 and through the communication interface 917, which communicate digital data with the computer system 900, are exemplary forms of carrier waves bearing the information and instructions.

The computer system 900 can send messages and receive data, including program code, through the network(s), the network link 919, and the communication interface 917. In the Internet example, a server (not shown) might transmit requested code belonging to an application program for implementing an embodiment of the present invention through the network 925, the local network 921 and the communication interface 917. The processor 903 may execute the transmitted code while being received and/or store the code in the storage device 909, or other non-volatile storage for later execution. In this manner, the computer system 900 may obtain application code in the form of a carrier wave.

The term "computer-readable medium" as used herein refers to any medium that participates in providing instructions to the processor 905 for execution. Such a medium may take many forms, including but not limited to non-volatile media, volatile media, and transmission media. Non-volatile media include, for example, optical or magnetic disks, such as the storage device 909. Volatile media include dynamic memory, such as main memory 905. Transmission media include coaxial cables, copper wire and fiber optics, including the wires that comprise the bus 901. Transmission media can also take the form of acoustic, optical, or electromagnetic waves, such as those generated during radio frequency (RF) and infrared (TR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the present invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

While the present invention has been described in connection with a number of embodiments and implementations, the present invention is not so limited but covers various obvious modifications and equivalent arrangements, which fall within the purview of the appended claims.

What is claimed is:

1. A method, comprising:
receiving inputs from a plurality of users, the inputs specifying one or more physical activities;
analyzing the inputs to quantitatively compare the activities among the users;
assigning a score to each user based on the analysis;
presenting the scores to the users over a communication network; and
comparing the scores on a normalized scale,
wherein the comparison step comprises assigning a base point value for an activity performed over a predefined period of time, base point values are adjusted for the relative skill of a particular user, and the adjustment comprises adjusting a number of sets of the activity performed by an intensity multiplier to arrive at an assigned point value per activity completed.

2. The method of claim 1, wherein the users utilize either a telephony device, a mobile device, or a computer to provide the inputs.

3. A method of fitness analysis comprising:
receiving inputs from a plurality of users, the inputs specifying one or more physical activities;
analyzing the inputs to quantitatively compare the activities among the users;
assigning a score to each user based on the analysis;
presenting the scores to the users over a communication network; and
comparing the scores on a normalized scale,
wherein the comparison step comprises assigning a base point value for an activity performed over a predefined period of time, base point values are adjusted for the relative skill of a particular user, and the adjustment comprises adjusting a relative length of time engaged in an activity by an intensity multiplier to arrive at an assigned point value per activity completed.

4. The method of claim 3, wherein the comparison step comprises a comparison between a user's performance and the user's historical performance.

5. The method of claim 3, wherein the comparison step comprises a comparison between a user's performance and the performance of other users.

6. The method of claim 3, wherein base point values are assigned by learning the base point values using previously entered aggregated data.

7. A method comprising:
accessing a fitness analysis system for recording a user's activity;
receiving numerical points responsive to an amount of effort exerted by the user in a particular activity;
assigning additional points based on dietary behavior and lifestyle;
grouping selected users into teams;
totaling the number of points earned by all of the users on each individual team during a predetermined period of time; and
comparing the total number of points earned by each team during the predetermined period of time to determine a winning team.

8. The method of claim 7, further comprising:
displaying a user's point totals relative to the user's historical performances; and
displaying other users' point totals relative to the other users' historical performances.

* * * * *